(12) United States Patent
Foust et al.

(10) Patent No.: US 11,534,514 B2
(45) Date of Patent: Dec. 27, 2022

(54) AQUEOUS OZONE GENERATOR CARTRIDGE WITH A WATER TREATMENT MANIFOLD

(71) Applicant: 3Oe Scientific, LLC, Carmel, IN (US)

(72) Inventors: Thomas F. Foust, Carmel, IN (US); Christopher Thompson, Fort Worth, TX (US); John Morici, Kildeer, IL (US); Anthony Casaletto, McHenry, IL (US)

(*) Notice: Subject to any disclaimer, the term of this patent is extended or adjusted under 35 U.S.C. 154(b) by 9 days.

(21) Appl. No.: 17/384,685

(22) Filed: Jul. 23, 2021

(65) Prior Publication Data

US 2022/0024795 A1 Jan. 27, 2022

Related U.S. Application Data

(60) Provisional application No. 63/056,538, filed on Jul. 24, 2020, provisional application No. 63/056,299, filed on Jul. 24, 2020.

(51) Int. Cl.
*A61L 2/18* (2006.01)
*C02F 1/00* (2006.01)
(Continued)

(52) U.S. Cl.
CPC ............ *A61L 2/183* (2013.01); *A61L 2/0088* (2013.01); *A61L 2/0094* (2013.01); *A61L 2/202* (2013.01); *A61L 2/26* (2013.01); *C02F 1/008* (2013.01); *C02F 1/4672* (2013.01); *C02F 1/46104* (2013.01); *C02F 1/78* (2013.01); *A61L 2202/11* (2013.01); *A61L 2202/122* (2013.01); *A61L 2202/14* (2013.01); *A61L 2202/15* (2013.01);
(Continued)

(58) Field of Classification Search
CPC ...... C02F 1/46; C02F 1/32; C02F 1/72; C02F 1/78
See application file for complete search history.

(56) References Cited

U.S. PATENT DOCUMENTS

| 3,421,999 A | 1/1969 | Corwin |
| 4,179,616 A | 12/1979 | Coviello et al. |

(Continued)

FOREIGN PATENT DOCUMENTS

| BR | 112014013734 | 6/2017 |
| CA | 2856196 | 6/2013 |

(Continued)

OTHER PUBLICATIONS

Cleancore Solutions; CCS1000 Ice System; Technical Data Sheet; https:cleancoresol.com/wp-content/uploads/2019/10/19-CCS1000-IceMachine.pdf; Jun. 4, 2020.

Panasonic Key Technologies; Boasting Hight Efficiency Makes It Possible to Miniaturize "Ozone Water" Device; Newsletter Accessed Jul. 19, 2021.

(Continued)

*Primary Examiner* — Cameron J Allen
(74) *Attorney, Agent, or Firm* — Innovation Law Office; Dennis S. Schell

(57) ABSTRACT

An illustrative expendable or reconstructable ozone generator cartridge for an aqueous ozone delivery device, for example, for antimicrobial sanitizing and/or medical treatment, includes a housing for a water treatment manifold providing parallel and operably fixed water pathways through ozone generating cells coupled to the manifold, and optionally a data logging and authentication feature.

23 Claims, 11 Drawing Sheets

(51) Int. Cl.
*C02F 1/461* (2006.01)
*C02F 1/467* (2006.01)
*C02F 1/78* (2006.01)
*A61L 2/00* (2006.01)
*A61L 2/20* (2006.01)
*A61L 2/26* (2006.01)

(52) U.S. Cl.
CPC ..... *A61L 2202/17* (2013.01); *C02F 2201/004* (2013.01); *C02F 2201/006* (2013.01); *C02F 2201/4614* (2013.01); *C02F 2201/4616* (2013.01); *C02F 2201/46135* (2013.01); *C02F 2201/46145* (2013.01); *C02F 2201/782* (2013.01); *C02F 2209/006* (2013.01); *C02F 2209/03* (2013.01); *C02F 2209/04* (2013.01); *C02F 2209/23* (2013.01); *C02F 2209/40* (2013.01); *C02F 2303/04* (2013.01)

(56) References Cited

U.S. PATENT DOCUMENTS

| | | |
|---|---|---|
| 4,200,121 A | 4/1980 | Walter et al. |
| 5,695,091 A | 12/1997 | Winnings et al. |
| 5,762,787 A | 6/1998 | Park et al. |
| 5,779,865 A | 7/1998 | Schulze et al. |
| 6,115,862 A | 9/2000 | Cooper et al. |
| 6,135,146 A | 10/2000 | Koganezawa et al. |
| 6,491,879 B2 | 12/2002 | Conrad |
| 6,706,243 B1 | 3/2004 | Sias et al. |
| 7,713,336 B2 | 5/2010 | Hengsperger et al. |
| 9,486,817 B2 | 11/2016 | Patton et al. |
| 9,919,939 B2 | 3/2018 | Rosko et al. |
| 10,640,878 B2 | 5/2020 | Jonte et al. |
| 10,767,270 B2 | 9/2020 | Jonte et al. |
| 10,900,921 B2 | 1/2021 | Brondum et al. |
| 10,947,138 B2 | 3/2021 | Rosko et al. |
| 2002/0185423 A1 | 12/2002 | Boyd et al. |
| 2006/0027507 A1 | 2/2006 | Hensperger et al. |
| 2006/0213924 A1 | 9/2006 | Ophardt |
| 2008/0227680 A1 | 9/2008 | Lynn |
| 2008/0237368 A1 | 10/2008 | Hengsperger et al. |
| 2010/0252415 A1 | 10/2010 | Lynn |
| 2010/0326472 A1 | 12/2010 | Glenn et al. |
| 2011/0011736 A1 | 1/2011 | Yost, III et al. |
| 2011/0247974 A1 | 10/2011 | Gale et al. |
| 2012/0285825 A1 | 11/2012 | Benedetto |
| 2013/0031799 A1 | 2/2013 | Gagnon et al. |
| 2013/0119083 A1 | 5/2013 | Ophardt et al. |
| 2013/0183749 A1 | 7/2013 | Aamodt et al. |
| 2013/0195725 A1 | 8/2013 | Lynn |
| 2013/0206654 A1* | 8/2013 | Lutz ................ C25B 9/00 210/85 |
| 2013/0224072 A1 | 8/2013 | Glazer et al. |
| 2014/0027388 A1 | 1/2014 | Constant |
| 2014/0263689 A1 | 9/2014 | Patton et al. |
| 2015/0308091 A1 | 10/2015 | Foust et al. |
| 2015/0335775 A1 | 11/2015 | Toso |
| 2016/0339132 A1 | 11/2016 | Cosman et al. |
| 2017/0137953 A1 | 5/2017 | Jonte et al. |
| 2017/0260722 A1 | 9/2017 | Horwitz et al. |
| 2017/0275191 A1 | 9/2017 | Lutz et al. |
| 2018/0008734 A1 | 1/2018 | Andersen et al. |
| 2018/0214588 A1 | 8/2018 | Casares |
| 2018/0306430 A1 | 10/2018 | Weaver et al. |
| 2018/0334752 A1 | 11/2018 | Oyama et al. |
| 2019/0001006 A1 | 1/2019 | Rodenbeck et al. |
| 2019/0022263 A1 | 1/2019 | Quilici |
| 2019/0025273 A1 | 1/2019 | Brondum et al. |
| 2019/0030204 A1 | 1/2019 | Jurak et al. |
| 2019/0201566 A1 | 7/2019 | Hollst |
| 2019/0209719 A1 | 7/2019 | Andersen et al. |
| 2019/0255205 A1 | 8/2019 | Cosman et al. |
| 2019/0284066 A1 | 9/2019 | Mullen et al. |
| 2020/0263312 A1 | 8/2020 | Jonte et al. |
| 2021/0123875 A1 | 4/2021 | Brondum et al. |
| 2021/0140904 A1 | 5/2021 | Brondum et al. |
| 2021/0179461 A1 | 6/2021 | Rosko et al. |

FOREIGN PATENT DOCUMENTS

| | | |
|---|---|---|
| CA | 2992280 | 1/2017 |
| CA | 2946465 | 5/2017 |
| CA | 3007437 | 6/2017 |
| CA | 2846169 | 8/2018 |
| CH | 669116 | 2/1989 |
| CN | 201495127 | 6/2010 |
| CN | 201760242 | 3/2011 |
| CN | 103987664 | 8/2014 |
| CN | 204120920 | 1/2015 |
| CN | 104826224 | 8/2015 |
| CN | 106967994 | 7/2017 |
| CN | 108264023 | 7/2018 |
| CN | 108946913 | 7/2018 |
| CN | 208791269 | 4/2019 |
| CN | 209220534 | 8/2019 |
| CN | 210528559 | 8/2019 |
| CN | 111419689 | 7/2020 |
| CN | 211005645 | 7/2020 |
| CN | 211024277 | 7/2020 |
| CN | 211559865 | 9/2020 |
| CN | 213048748 | 4/2021 |
| CN | 213231656 | 5/2021 |
| CN | 213251572 | 5/2021 |
| DE | 29518833 | 9/1996 |
| DE | 202020003223 | 8/2020 |
| ES | 1111506 | 11/2011 |
| GB | 767227 | 1/1957 |
| JP | 2002146865 | 11/2000 |
| JP | 2008189968 | 8/2008 |
| JP | 4528840 | 8/2010 |
| JP | 5574877 | 8/2014 |
| JP | 2014201768 | 10/2014 |
| JP | 5925653 | 5/2016 |
| KR | 20110039612 | 4/2011 |
| KR | 101211390 | 12/2012 |
| KR | 101367624 | 3/2014 |
| KR | 20200104630 | 9/2020 |
| KR | 102180182 | 11/2020 |
| KR | 20090045482 | 11/2020 |
| WO | 2011144285 | 11/2011 |
| WO | 2013086217 | 6/2013 |
| WO | 2016210071 | 12/2016 |
| WO | 2017011506 | 1/2017 |
| WO | 2017112795 | 6/2017 |
| WO | 2018100358 | 6/2018 |
| WO | 2021036087 | 3/2021 |

OTHER PUBLICATIONS

Meritech, CleanTech Automatic Hand Washing Stations; Retrieved from webpage <https://www.meritech.com/products/handwashing-systems>; Jul. 19, 2021.

Cashido; 10 Second Machine Product Page; Retrieved from the webpage <https://www.cashido.com.tw/en/product/10-Second-Machine/ozone-faucet.html>; Jul. 19, 2021.

Oxidation Technologies, LLC—SB100 Product Page; Retrieved from webpage <https://www.oxidationtech.com/sb100.html>; Jul. 19, 2021.

Deposon; Ozone Sanitizing Sprayer Product Page; Retrieved from webpage <https://www.deposon.com/Ozone-Sanitizing-Sprayer-pd49322496.html>; Jul. 19, 2021.

Panasonic; YouTube video illustrating the structure of Panasonic's "Ozone Water" device; Retrieved from <https://www.youtube.com/watch?v=ckZPjSygOOc>; Jul. 19, 2021.

Diamonox Advanced Diamond Technologies; Ozone Generator G3 Product page; Downloaded Feb. 17, 2020.

Diamonox Advanced Diamond Technologies; Ozone Generator Mini product page; Downloaded Feb. 17, 2020.

Diamonox Advanced Diamond Technologies; Ozone; Product Page; Downloaded Feb. 17, 2020.

(56) References Cited

OTHER PUBLICATIONS

Advanced Diamond Technologies, Inc.; UNCD Electrodes; Technical Performance Data.
Robert B Raffa, Joseph V. Pergolizzi, Robert Taylor, Sanjib Choudhuri and Robert Rodenbeck; Scientific Research Publishing—Persistence of Healthcare-Associated (Nosocomial) Infections Due to Inadequate Hand Hygiene: Part 1—Biological and Treatment Factors; Aug. 9, 2018.
Robert B Raffa, Joseph V. Pergolizzi, Robert Taylor, Sanjib Choudhuri and Robert Rodenbeck; Scientific Research Publishing—Persistence of Healthcare-Associated (Nosocomial) Infections Due to Inadequate Hand Hygiene: Part 2—Human Factors; Aug. 10, 2018.
Robert B Raffa, Joseph V. Pergolizzi, Robert Taylor, Sanjib Choudhuri, and Robert Rodenbeck; Scientific Research Publishing—Persistence of Healthcare-Associated (Nosocomial) Infections Due to Inadequate Hand Hygiene: Part 3—Application of Human Factors Engineering to an Ozone Hand Sanitizer; Aug. 10, 2018.
Search Report and Written Opinion issued for PCT/US21/43084 dated Nov. 1, 2021.
Search Report and Written Opinion issued for PCT/US21/043092 dated Nov. 3, 2021.
Search Report and Written Opinion issued for PCT/US21/43079 dated Dec. 28, 2021.
Search and Written Opinion issued for PCT/US21/43069 dated Oct. 29, 2021.
Search and Written Opinion issued for PCT/US21/43066 dated Oct. 29, 2021.
Search and Written Opinion issued for PCT/US21/43091 dated Jan. 31, 2022.

* cited by examiner

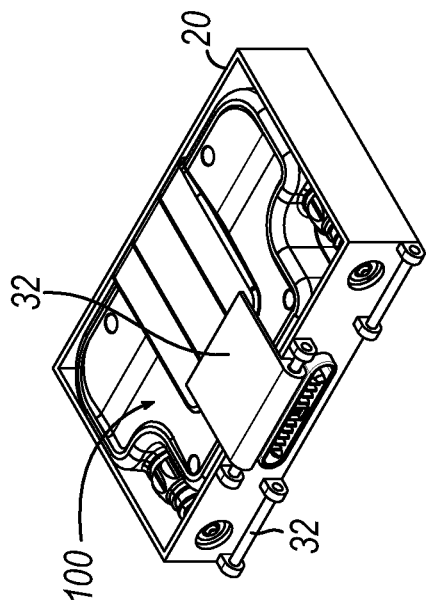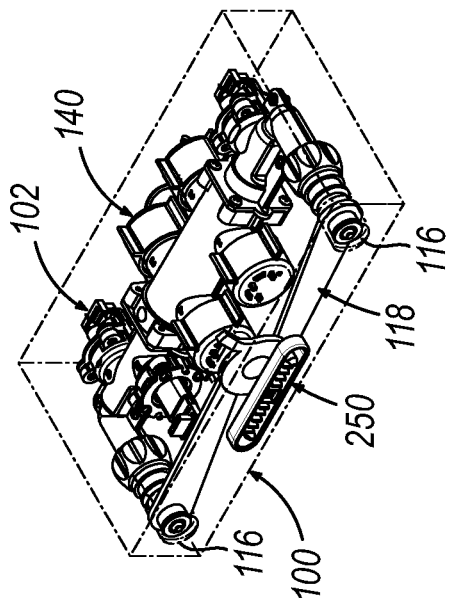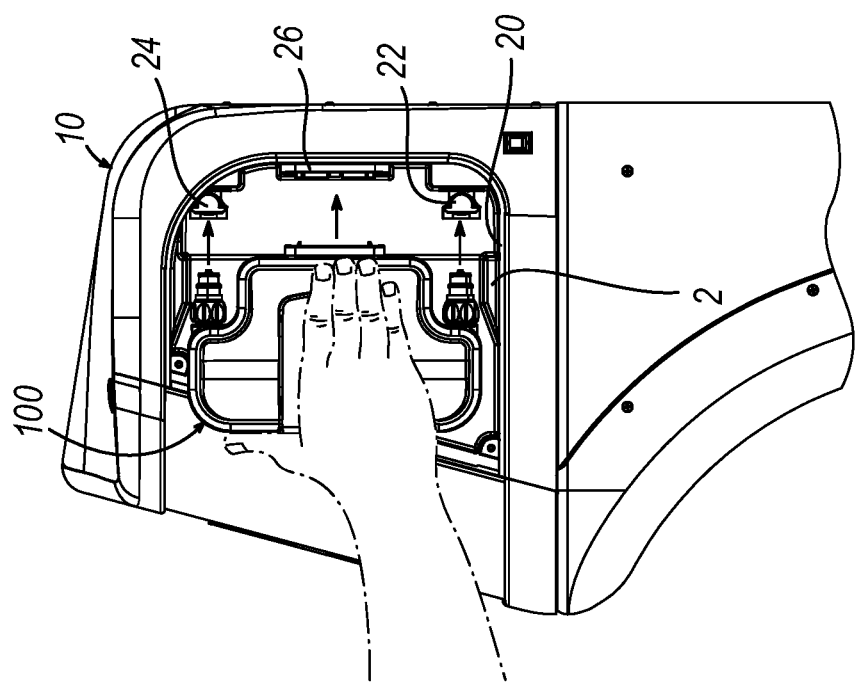

AQUEOUS OZONE GENERATOR CARTRIDGE WITH A WATER TREATMENT MANIFOLD

CROSS-REFERENCE TO RELATED APPLICATION

This is a nonprovisional patent application of U.S. Provisional Patent Application No. 63/056,299, filed Jul. 24, 2020, and titled Aqueous Ozone Sanitizing System; and U.S. Provisional Patent Application No. 63/056,538, filed Jul. 24, 2020, and titled Ozone Generator Cartridge for Ozonating Water; each of which are incorporated herein by reference.

BACKGROUND

The present invention relates to a device for adding ozone to water, and particularly, to a device to ozonate a water supply stream to a desired concentration.

Ozone ($O_3$) is known to be a highly effective disinfectant. Ozone is produced when water ($H_2O$) or oxygen ($O_2$) is energized, producing monatomic ($O_1$) molecules that collide with oxygen ($O_2$) molecules to for ozone ($O_3$). The third oxygen atom in ozone is loosely bonded and is therefore highly reactive and readily attaches to and oxidizes other molecules. When used to sterilize, exposure to ozone has been demonstrated to be very effective at killing microorganisms, including bacteria, viruses, and spores.

Aqueous ozone, a solution of water ($H_2O$) and ozone ($O_3$), has also been demonstrated to be effective at sanitizing, i.e., killing microorganisms, when applied at a sufficient combination of ozone concentration and exposure time. Example applications for sanitizing using aqueous ozone include hand sanitizing in place of a soap or other disinfectant wash, the clinical treatment of infected tissue, sanitizing food, and sanitizing medical, food processing, and other instruments and work surfaces.

A concern noted regarding the use of ozone for hand and other tissue sanitizing is the potential adverse effect to human or animal cells if applied at too high of an ozone concentration or for an exposure that is too prolonged, e.g., the 'dosage.' It is known that very high doses of ozone can cause lung and other tissue damage. On the other hand, mild to moderate oxidative cell stress caused by low doses of ozone appears to be suggest a therapeutic effect that benefits and aids tissue healing. While it remains unclear how high a level of exposure would lead to unintended cellular damage or clinically relevant skin pathologies, safety warrants using only the ozone dosage required to achieve the desired logarithmic level of reduction of the targeted microorganisms, which is also expected to be proven to be of little risk and likely therapeutic benefit to human tissue. Many prior art systems provide aqueous ozone by generating ozone gas from air, which has lower concentrations of oxygen molecules than water, or from liquid oxygen, which is expensive and difficult to handle logistically and in the process. Further, once gaseous ozone is produced, it must be uniformly distributed and dissolve, which is difficult and inefficient, requiring a number of controlled process steps and often producing excess ozone off-gas and non-uniform distribution of dissolved ozone in the water stream. For the smaller scale of a device or other appliance, for example, for a single user, gaseous generation and mixing effective and efficient for an industrial or municipal scale is not practically applied from a cost, technological, or effectiveness perspective.

In light of the need for well-regulated dosage, a high level of assurance must be incorporated into generating and delivering the desired level of aqueous ozone concentration and exposure time that is effective at killing targeted microorganisms while not inducing undue oxidative stress to the hands (dermis cells) or other tissues being sanitized. The present disclosure is a result of the recognition of and response to the need for improved generation and delivery systems for aqueous ozone sanitizing.

SUMMARY

The present invention may comprise one or more of the features recited in the attached claims, and/or one or more of the following features and combinations thereof.

An illustrative expendable or reconstructable ozone generator cartridge for an aqueous ozone delivery device, for example, for antimicrobial sanitizing and/or medical treatment, includes a housing for a water treatment manifold providing parallel and operably fixed water pathways through ozone generating cells coupled to the manifold, and optionally a data logging and authentication feature.

Embodiments according to the present disclosure advantageous produce aqueous ozone directly by electrolytic action within a water stream, thereby cost and process efficiently and effectively producing uniformly dissolved ozone in water (aqueous ozone) with minimal off-gassing. The embodiments used with illustrative devices disclosed herein further produce and deliver the aqueous ozone in a small compact space, minimizing ozone decay in application, and maximizing the rinsing and sanitizing effects of both chemical and mechanical action with a high surface area provided by small uniform particles of aqueous ozone with a high spin rate, applied by direct irrigation to the entire surface of the hands, efficiently loosening and lessening the microbe load.

While not limited to this application and concentration or kill rate, embodiments used with an illustrative sanitizing device disclosed herein may be used to sanitize a user's hands with a 0.8 ppm concentration of aqueous ozone at a flowrate of about 3.0 gallons per minute for a duration of 7 seconds, which has been demonstrated with the illustrative embodiment to have a antimicrobial effect of providing at least a minimum of a 3 log reduction in the broad spectrum of microorganisms that typical sanitization systems kill (for example, Tentative Final Monograph (TFM) 24), including for example, clostridioides difficile (C. diff).

Additionally, embodiments disclosed herein can provide up to a 4.0 ppm concentration of aqueous ozone over different periods of time and different flowrates to meet the needs of various applications and uses. In some embodiments the ozone generator cartridge and sanitizer may be configured and used to operate as a wellness rinse without specific healthcare or medical disinfection performance criteria standards or approvals, and in other embodiments the sanitizer may be configured and used to operate as a medical device in a healthcare environment, including for example, for treatment and/or sterilization, with appropriate governmental and/or industry approvals and performance criteria standards, including, for example, with other body parts, tissue, or objects, including instruments.

An illustrative embodiment of an aqueous ozone generator cartridge, comprises: a water inlet for supplying water to the cartridge; a water outlet for expelling aqueous ozone from the cartridge; a water treatment manifold including a coaxial water passageways portion having an inner conduit located within an outer conduit, one of the inner and outer conduits fluidly coupled to the water inlet, and the other of the inner and outer conduit fluidly coupled to the water outlet; and at least one ozone generating cell having a generating portion located outside the inner conduit and fluidly coupled with the inner and outer conduits to enable the manifold to provide waterflow through the generating portion of each of the at least one ozone generating cells.

Additionally or alternatively, in any subcombination, wherein the manifold defines:

a flow separation chamber to supply a plurality of water pathways through the at least one ozone generating cells; and a flow confluence chamber to rejoin the plurality of water pathways into a single water pathway; wherein the manifold and the at least one ozone generating cells together define parallel water pathways whereby waterflowing from the water inlet to the water outlet passes through only one of the at least one ozone generating cells; wherein the inner and outer conduits each define a plurality of pairs of openings for fluidly coupling the at least one ozone generating cells; wherein at least two pairs of the plurality of pairs of openings are angularly displaced along the same circumferential arc of the coaxial water passageways portion, thereby minimizing a length of the manifold; wherein at least one of the plurality of pairs of openings is populated with a fluidly sealing plug instead of one of the at least one ozone generating cells; wherein a plurality of water pathways defined between the water inlet and the water outlet are operably fixed; wherein: each of the at least one ozone generating cells includes a cell inlet for receiving water, each cell inlet is fluidly coupled to a space between the inner and outer conduits; and each of the at least one ozone generating cells includes a cell outlet for expelling water, each cell inlet is fluidly coupled to the inner conduit; wherein: the space between the inner and outer conduits defines an annulus fluidly coupled to the water inlet; and the inner conduit is fluidly coupled to the water outlet; wherein the only fluid coupling defining water pathways between the annulus and the inner conduit each pass through one of the at least one ozone generating cells; wherein the inner conduit includes a baffle to reduce waterflow turbulence; wherein the orientation of the baffle is nonorthogonal relative to ozonated water flowing from each of the at least one ozone generating cell and into the inner conduit; wherein the baffle is a divider fluidly separating at least a portion of the length of the inner conduit into a first flow area and a second flow area, whereby each of the first and second flow areas receive ozonated waterflow from a subset of the at least on ozone generating cells.

Additionally or alternatively, in any subcombination, further comprising a first oxidation-reduction potential sensor fluidly coupled to the manifold and located between the coaxial water passageways portion of the manifold and the water outlet; further comprising a second oxidation-reduction potential sensor fluidly coupled to the manifold and located between the coaxial water passageways portion of the manifold and the water inlet; further comprising a housing, and wherein the housing encloses the manifold, the at least one ozone generating cells, and first and second oxidation reduction potential sensors; further comprising a third oxidation-reduction potential sensor fluidly coupled to manifold and located between the first oxidation-reduction potential sensor and the water outlet; further comprising a housing enclosing the water treatment manifold and the at least one ozone generating cell, and wherein the housing can be opened to reconstruct the aqueous ozone generator cartridge by replacing the at least one ozone generating cell.

An alternative illustrative embodiment of an aqueous ozone generator cartridge, comprises: an electrical connector; a water inlet for supplying water to the cartridge; a water outlet for expelling aqueous ozone from the cartridge; a water treatment manifold fluidly coupled to the water inlet and the water outlet; and at least one ozone generating cell located within the housing and having a generating portion receiving a power signal from the electrical connector and fluidly coupled with the water treatment manifold to provide a plurality of water pathways, each of the plurality of water pathways flows through the generating portion of only one of the at least one ozone generating cells; and wherein the plurality of water pathways are fluidly parallel and operably fixed.

Additionally or alternatively, in any subcombination, further comprising a first sensor fluidly coupled to the manifold, measuring an attribute of the water altered by the ozone generating cells, and providing a data signal to the electrical connector; further comprising a memory device enclosed by the housing and electrically coupled with the electrical connector and wherein the memory device enables at least one of cartridge usage data logging and storage of cartridge identity data; further comprising a security device authenticating at least one of a manufacturer and a reconstructor of the cartridge.

Yet another alternative illustrative embodiment of an aqueous ozone generator cartridge, comprises: a water inlet for supplying water to the cartridge; a water outlet for expelling aqueous ozone from the cartridge; a water treatment manifold including a coaxial water passageways portion having an inner conduit located within an outer conduit, one of the inner and outer conduits fluidly coupled to the water inlet, and the other of the inner and outer conduit fluidly coupled to the water outlet; and at least one ozone generating cell having a generating portion located outside the inner conduit and fluidly coupled with the inner and outer conduits to enable the manifold to provide waterflow through the generating portion of each of the at least one ozone generating cells; and wherein the water pathways between the water inlet and the water outlet are fluidly parallel and operably fixed.

For purposes of this disclosure, including the claims, the term 'about' is defined as within a definite range of +/−10% of the referenced value. Additional features of the disclosure will become apparent to those skilled in the art upon consideration of the following detailed description of the illustrative embodiment.

BRIEF DESCRIPTION OF THE DRAWINGS

The detailed description particularly refers to the accompanying Figs. in which:

FIG. 9 illustrates installation/removal of the ozone generator cartridge of FIG. 1 with a docking station of the ozone sanitizing device of FIGS. 2A and 2B;

FIG. 10 illustrates a release mechanism of the docking station of ozone sanitizing device of FIGS. 2A and 2B that is associated with the ozone generator cartridge of FIG. 1;

FIG. 11 illustrates a release mechanism of a second embodiment of an ozone generator cartridge according to the present disclosure.

DESCRIPTION OF THE ILLUSTRATIVE EMBODIMENTS

Figure 1:
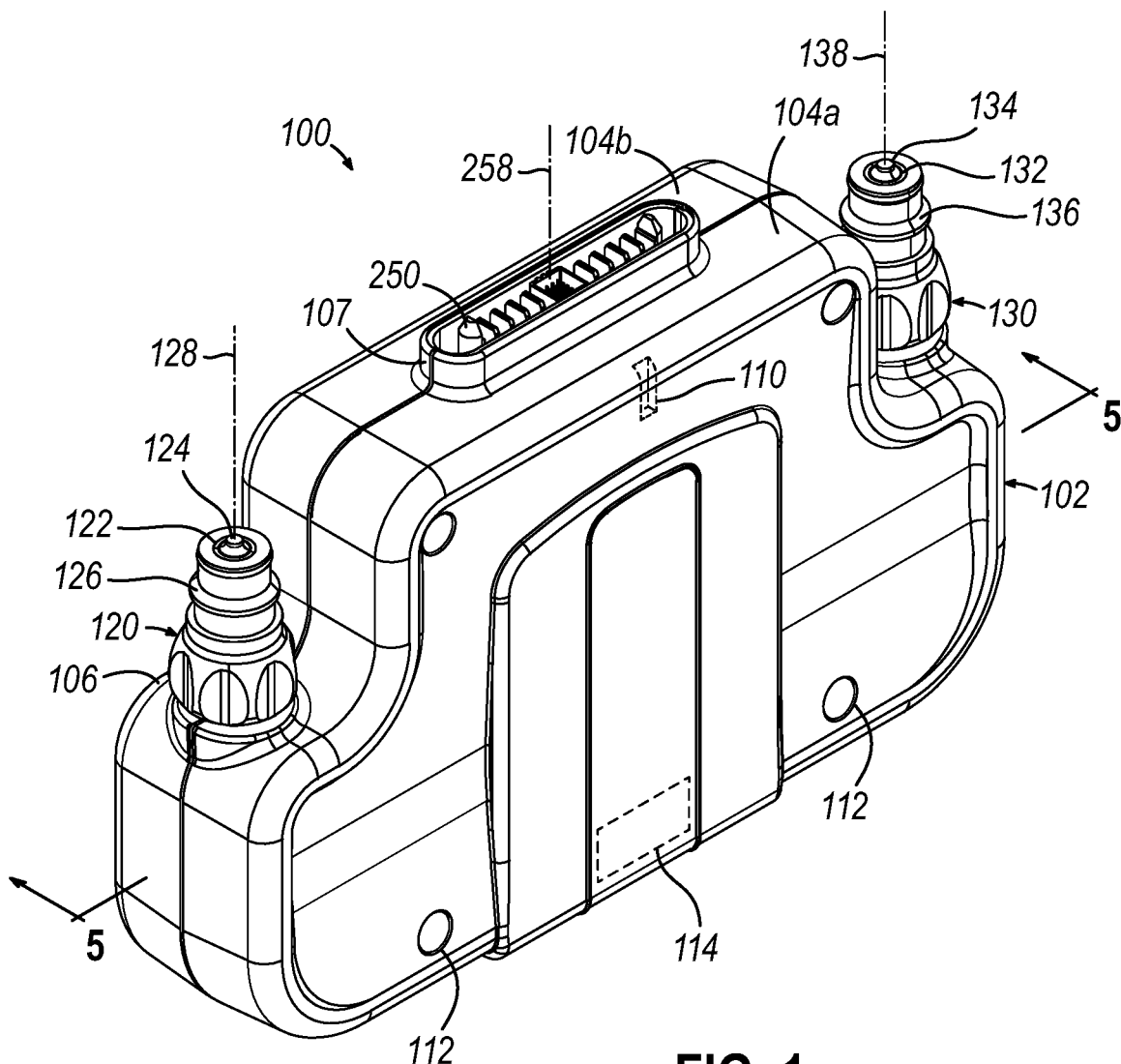
FIG. 1 is a perspective assembly view of a first embodiment of an ozone generator cartridge according to the present disclosure.

For the purposes of promoting and understanding the principals of the invention, reference will now be made to one or more illustrative embodiments shown in the drawings and specific language will be used to describe the same.

Figure 2B:
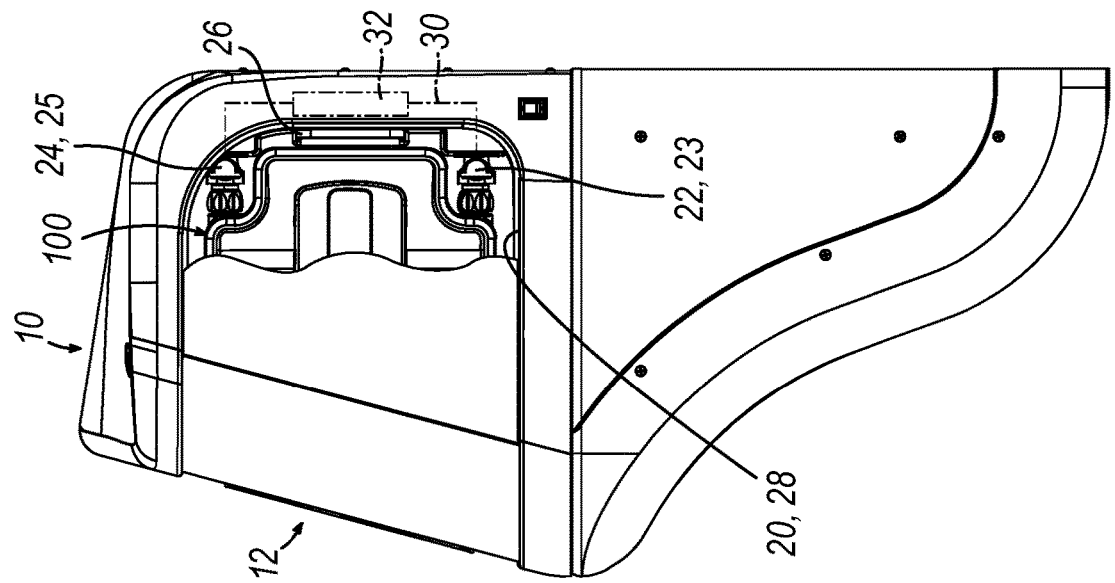
FIG. 2B is a side view of the aqueous ozone sanitizing device of FIG. 2A.
Figure 2A:
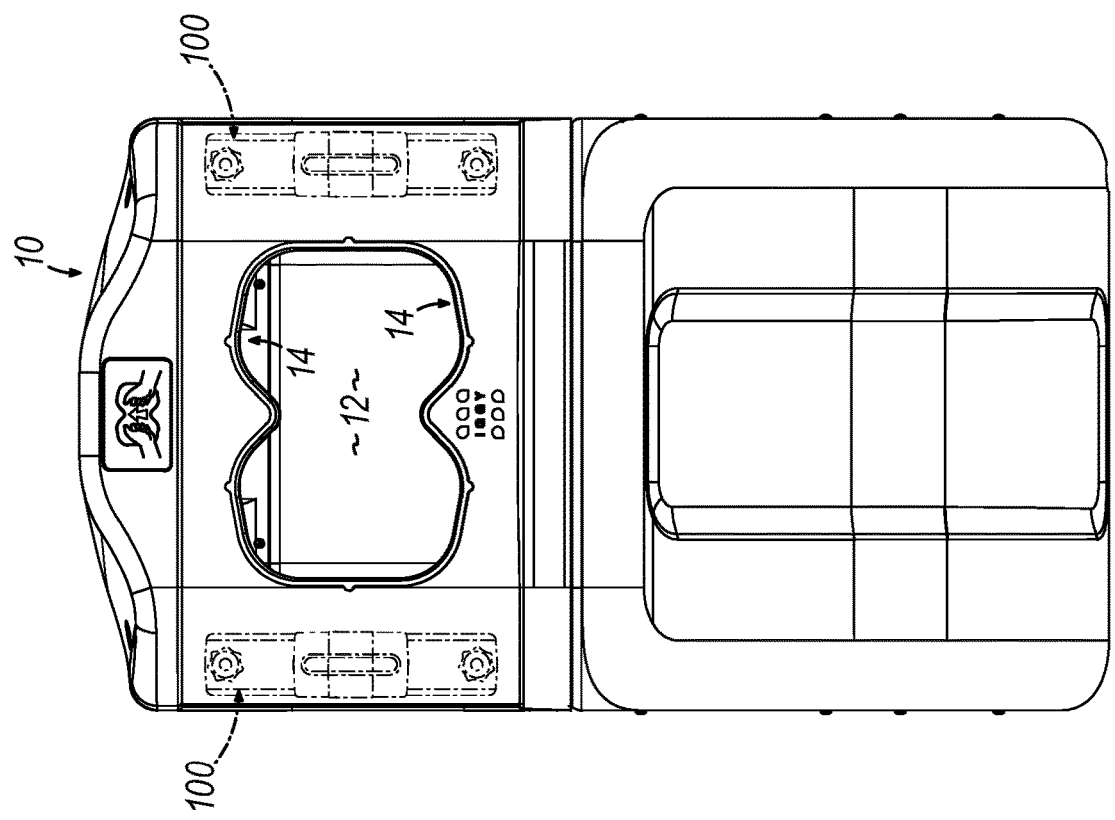
FIG. 2A is a front view of an aqueous ozone sanitizing device including a pair of ozone generator cartridges according to FIG. 1.

Referring to FIGS. 2A and 2B, an illustrative ozone generator cartridge 100 according to the present disclosure is illustrated. Referring to FIGS. 2A and 2B, the ozone generator cartridge 100 includes features described below that enable it to be plugged into a docking receptacle 20, also referred to as a docking station, of an ozone sanitation device 10, also referred to as an ozone dispensing device, in a single movement along a single axis. For example, not requiring rotation or twisting of the generator cartridge 100 or other components to fluidly and electrically engage and mechanically lock the cartridge 100 with the docking receptacle 20. While some prior art designs disclose individual generator cells and individual sensors capable of being unscrewed and replaced from a prior art system, generator cartridge 100 advantageously can provide one or more generator cells 210, sensors, and other electronic and mechanical devices discussed below in a single housing 102 and pluggable, docking form that can be removed and replaced with exposing sensitive surfaces of the components to potential damage upon removal or installation as in prior art systems.

The ozone sanitation device 10 for which cartridge 100 is designed to provide aqueous ozone may be, for example, a hand sanitizing unit or other sanitizing device, wherein sanitizing is understood to include simply rinsing or to include treatment.

While the illustrative embodiment discusses sanitizing of a user's hands, other embodiments within the scope of the claimed invention include sanitizing systems suitable for sanitizing other body parts, for example, hands and forearms or feet, and for sanitizing other objects, for example, including tools or instruments such as medical devices, so it is under stood that an object or a different body part or tissue can be substituted for all occurrences of the disclosure reciting 'a hand.'

Referring to FIG. 1, the ozone generator cartridge 100 receives untreated water supply 23 at a water inlet connector 120 and provides ozonated waterflow 25 at a water outlet connector 130. An electrical connector 250 connects power signals 260, sensor data signals 262, security data signals 264, and data logging signals 266, as will be described further below, with the ozone sanitation device 10. The connectors 120, 130, and 250 may be, for example, plastic and/or metal quick-disconnect connectors to facilitate the pluggable aspect of the cartridge 100, including auto-locking of mechanical features to retain the engaged position.

Figure 4:
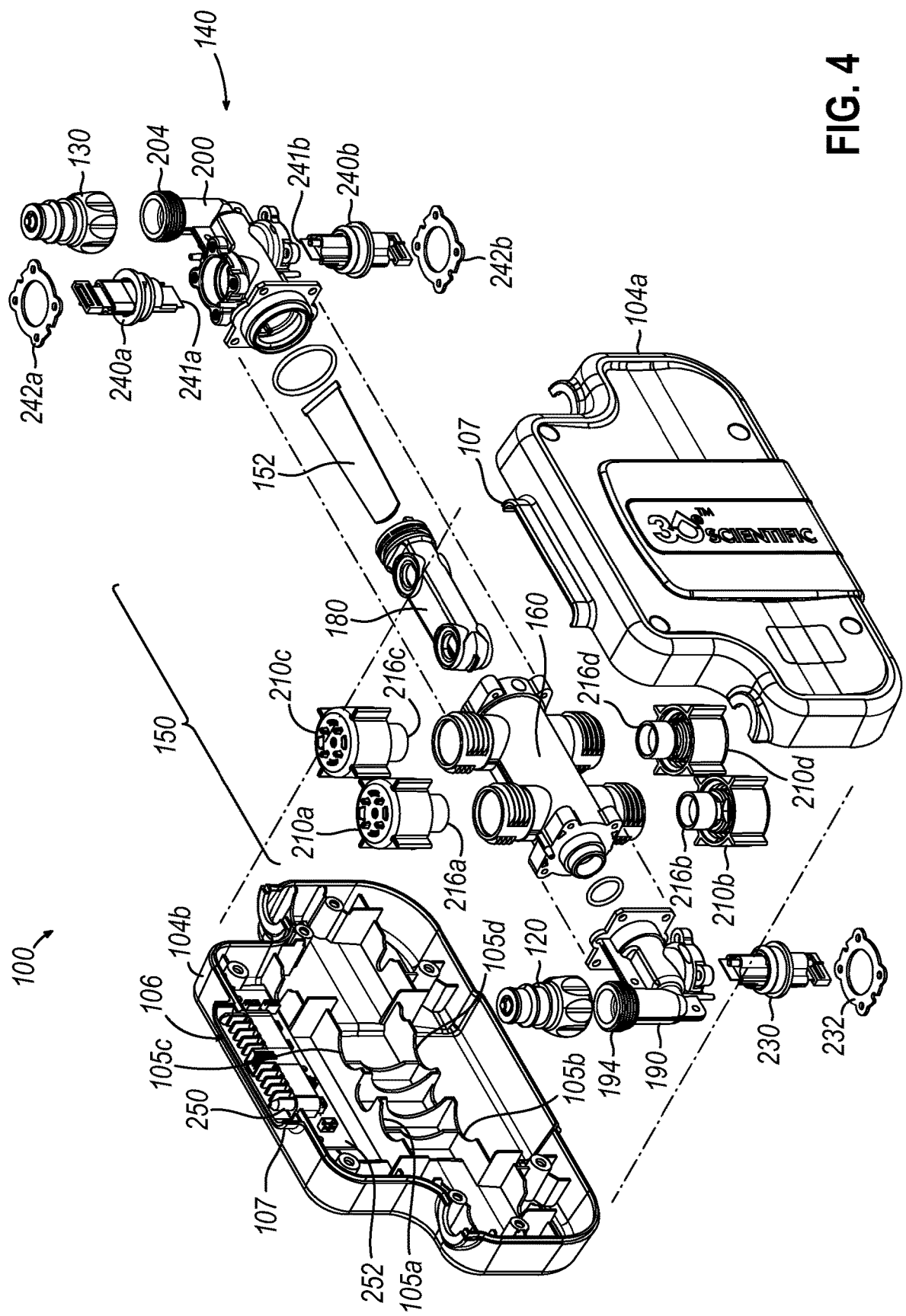
FIG. 4 is an exploded view of the ozone generator cartridge of FIG. 1.

Referring to FIG. 4, the housing 102 of the cartridge 100 may be formed from two or more releasable housing components, for example, housing sides 104a and 104b. The housing 102 provides structure to support the components of cartridge 100, and also secures sensitive internal components from damage and tampering that could inhibit safety and performance. The housing sides 104a and 104b may be formed from PVC or another molded or non-molded rigid material.

Figure 3:
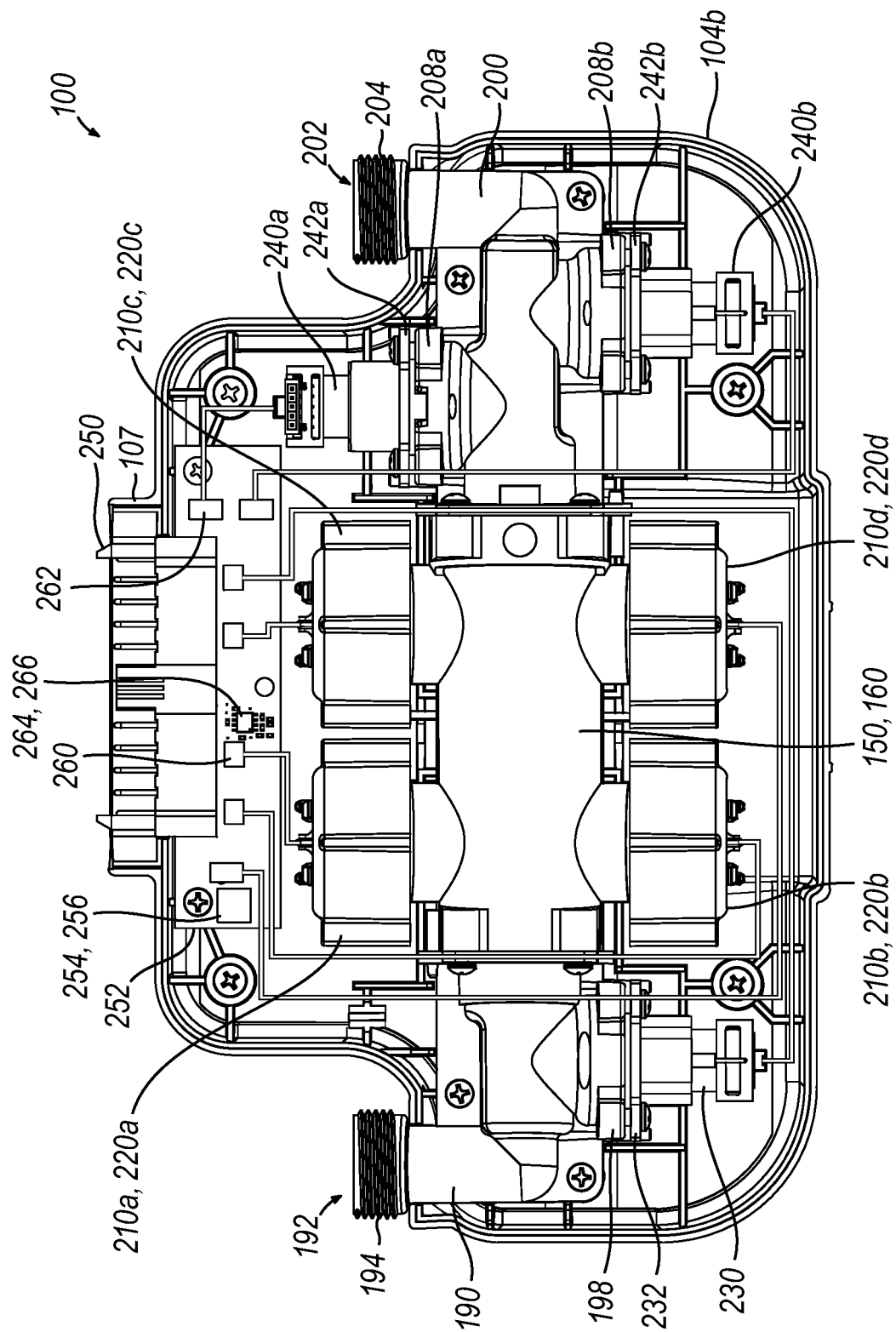
FIG. 3 is the ozone generator cartridge of FIG. 1 illustrated with one side housing removed.

Referring to FIG. 3, the cartridge 100 is shown with the housing side 104a removed to better illustrate the internal components of the cartridge 100, and the water connectors 120 and 130 are also removed. Referring to FIG. 4, the cartridge 100 is shown in exploded perspective view. Referring now to FIGS. 3 and 4, the cartridge 100a includes a manifold 140 that forms a water passageway 300 (FIG. 6) for waterflow and treatment between an inlet opening 192, at which the connector 120 may be attached, and an outlet opening 202, at which the connector 130 may be attached. The manifold 140 also mounts and fluidly couples with the water passageway 300 several water treatment devices 110, 230, and 240.

In the illustrative embodiment the manifold 140 and the water passageway 300 include a central water passageway portion 150 that is fluidly coupled between an inlet waterway passage portion 190 and an outlet water passageway portion 200. In the illustrated embodiment of the cartridge 100, ozone generating cells 210a-210d are mounted upon and fluidly coupled with the central water passageway portion 150, an inlet sensor 230 is mounted upon and fluidly couples with inlet water passageway portion 190, and outlet sensors 240a and 240b are mounted upon and fluidly coupled with the outlet water passageways portion 200.

Figure 6:
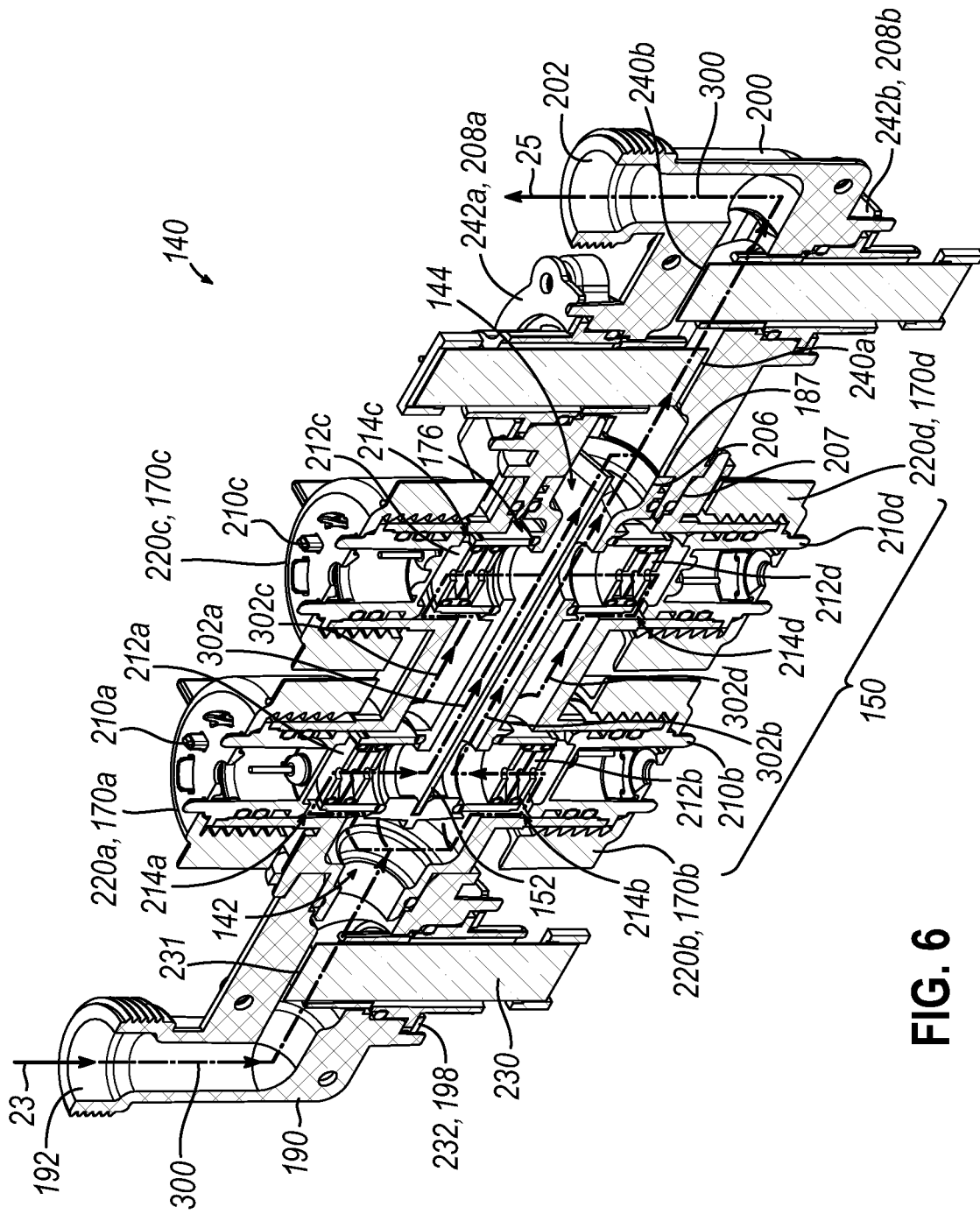
FIG. 6 is a portion of the ozone generator cartridge as illustrated in cross-section in FIG. 4 illustrating waterflow through the cartridge.

Referring to FIG. 6, in the illustrative embodiment, an untreated supply waterflow 23 provided to the cartridge 100 at an inlet opening 192 of the inlet water passage way portion 190 flows through an operably fixed (i.e., continuous, without valves or other actuators that operably change the flow) water passageway 300 formed by manifold 140, ultimately existing as ozonated waterflow 25 at an outlet opening 202 of the outlet water passageway portion 200. As will be further discussed below, the operably fixed water passageway 300 includes a series of parallel water passageways 302a-d that are enabled in part by a coaxial feature of the central water passageway portion 150.

Referring to FIG. 3, an electrical connector 250 is accessible from outside of the housing 102 and can be electrically coupled to or mounted on a circuit board 252. The circuit board 252 may include, for example, a memory device 254 and related electrical components, and a security device 256, which may be separate from or a function of the memory device 254. In the illustrative embodiment, control circuits and power supplies for the electrical components of the cartridge 100 are provided by the ozone sanitation device 10 via power signals 260 and sensor data signals 262; however, in an alternative embodiment, circuit board 252 my comprise these elements. For example, in one embodiment, the circuit board 252 includes a processor to perform functions discussed herein that are described as performed by either of the cartridge 100 or the ozone sanitation device 10.

Figure 5:
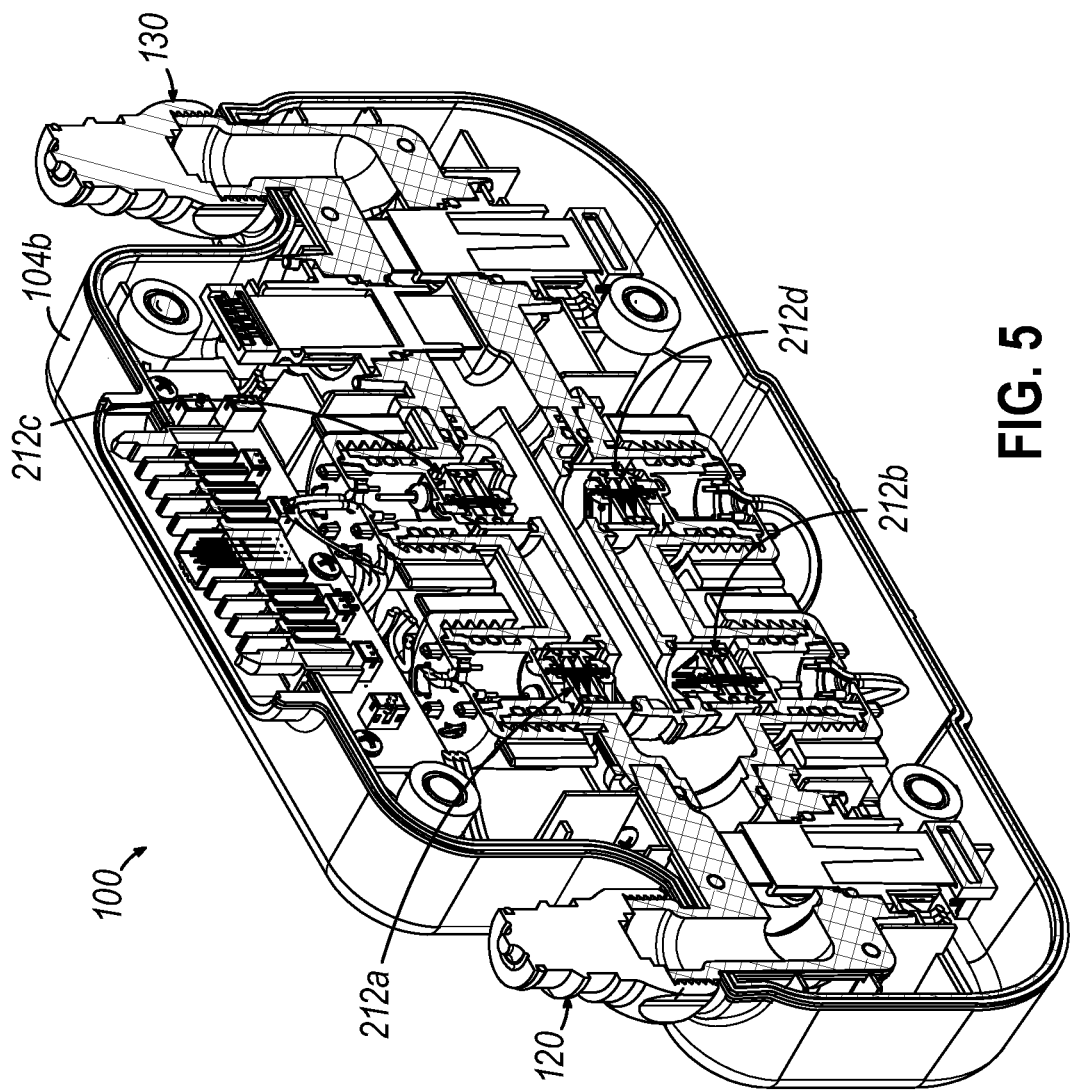
FIG. 5 is a cross-sectional view of the ozone generator cartridge of FIG. 1 taken along lines 5-5 shown in FIG. 1.

FIG. 5 is a cross-sectional assembly view taken along cross-section lines 5-5 illustrated in FIG. 1. While the below discussion will primarily reference FIGS. 6-8D, which are partial assembly perspective and cross-sectional views, FIG. 5 can be referred to for additional illustration of the arrangement of cartridge 100.

An inlet sensor 230 is in fluid communication with water passageway 300 within the inlet water passageway 190 of manifold 140. The inlet sensor 230 sensor provided measurement of an attribute, e.g. including a property or parameter, of the untreated supply waterflow 23 that will be altered by the ozone generating cells 210 effecting an increase in ozone concentration in the waterflow through the water passageway 300. For example, inlet sensor 230 may be an oxidation reduction potential (ORP) sensor that provides a baseline measurement that can be compared to a measurement of the ozonated waterflow 25 flow out of water passageway portion 150 of the manifold 140.

A change in oxidation-reduction potential (ORP) can be attributed to an increase in the ozone concentration in the water. An ozone concentration level can be determined by measuring the ORP downstream of the ozone generating cells 210a-d, and taking into account the ORP of the untreated water supply if known and consistent, or by actually measuring and taking into account the ORP upstream of the ozone generating cells 210a-d. The ozone concentration added to the water by the ozone generating cells 210a-d can be calculated as a function of the differential in upstream and downstream ORP measurements.

The inlet sensor 230 can comprise at least a pair of electrodes, a working electrode and a reference electrode, or alternatively, a set of three electrodes, a counter electrode, a working electrode, and a reference electrode, carried by one or more non-conductive substrates, such as silicone or glass, supported by a housing and exposed to the waterflow. The reference electrode uses an inert metal, for example, gold, platinum, silver or a chloride molecule thereof, which resist chemical action and corrosion, but will lose electrons to an oxidant such as ozone until its potential reaches that of the ORP level of the water. By comparing a constant potential established between the working electrode and counter electrode pair, which is not affected by change in ORP, with the potential of the reference electrode, which is, the ORP of the water is determined. The conversion from difference in potential to the concentration of ozone can be made based on a calibration factor or look up table for the electrode set developed using a solution of known ozone concentration.

The sensor 230 and sensor 240a-b discussed below may be, for example, one of the sensor configurations disclosed by US Patent Publication 2016/0209346 published Jul. 21, 2016, which is hereby incorporated herein by reference, or the commercially available electrode sensor part numbers such as RRPX020AU and RREFX103 or RRPE100XC and RRPEAGCL from Pine Research of Durham, N.C.

In some embodiments, sensors 230 and 240a-b may additionally or alternative include other quality sensing elements on a single or multiple substrates for temperature, flow, conductivity, acidity, and other such attributes (e.g. parameters and properties) of water or of the devices operating with the cartridge 100. Of note, for typical applications discussed herein, various of these other listed attributes in most municipal water supplies do not appear to have a significant bearing on the amount of ozone produced, or the amount of decay in a brief distance and time for the typical applications, so it is contemplated that measure or control is not required for many of the applications and uses discussed here.

Figure 7:
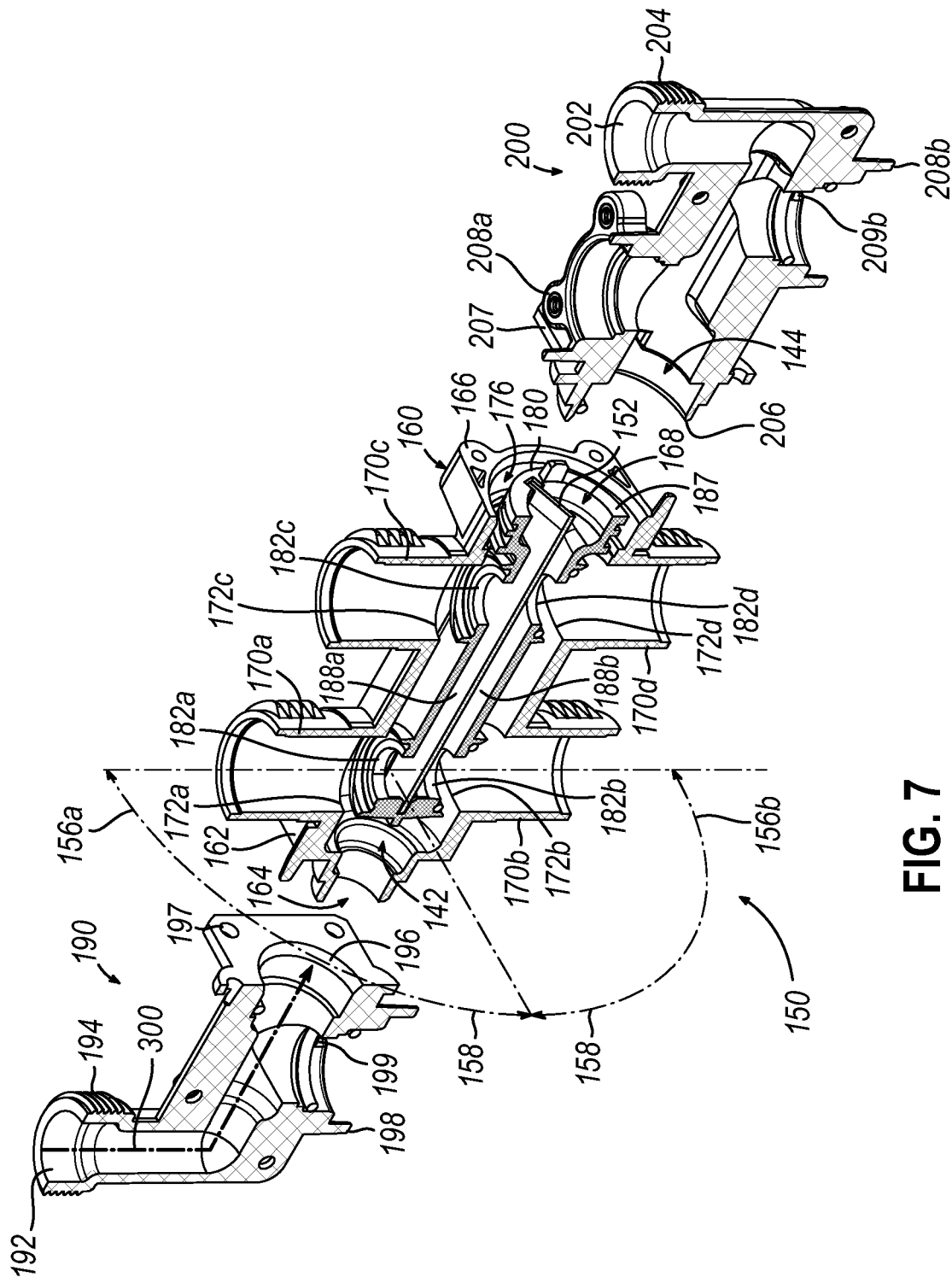
FIG. 7 is an exploded cross-sectional view of the manifold portion of the ozone generator cartridge as illustrated in cross-sectional view in FIG. 4.

Referring to FIGS. 6 and 7, from outlet opening 196 of the inlet water passageway portion 190 of manifold 140, the water passageway 300 extends through inlet opening 164 and into a flow separation chamber 142 defined by the central water passageway portion 150. In the illustrated embodiment, the waterway passageway portion 150 includes an internal conduit 180 located coaxially within outer conduit 160, thereby defining a coaxial arrangement and parallel flow feature of manifold 140. The functions of the central water passageway portion 150 include exposing the waterflow through water passageway 300 to the ozone generating cells 210a-d, thereby increasing the ozone concentration of the waterflow, and minimizing the length of water passageway 300 and minimizing changes in water pressure, velocity, vortices, and other flow disturbances, all of which all to the reduce ozone concentration of the waterflow.

Each ozone generating cell 210a-d includes a generating portion 212a-d as well as a housing, fluid pathways, and/or other support structure. An exemplary generating portion 212a-d includes a pair of electrode plates (an anode and a cathode) having slots defined therethrough for the flow of water, hydrogen, oxygen, and ozone. The electrodes can be constructed of boron-doped silicone and coated with boron-doped diamond, for example, using chemical vapor deposition. Power can be applied from all edges of the electrodes to maximize ozone production. The electrodes can be separated by a thin membrane that allows proton exchange therethrough, and for example a solid polymer electrolyte such as a polytetrafluoroethylene(PTFE)/perfluorosulfonic acid (PFSA) copolymer membrane, which is commercially available from The Chemours Company of Wilmington, DE as NAFION (trademark of The Chemours Company FC, LLC).

As is discussed further below, each of the parallel water passageways 302a-d of the present disclosure can provide a waterflow across each oppositely charged electrode plate, for example, across the electrode surface on the side opposite the separation membrane, resulting in the production of ozone within the water. The thin separation membrane located between electrode plates, for example, 20-30 microns thick, may also allow for some cross-diffusion of water, hydrogen, and oxygen molecules.

The concentration of ozone developed by the generating cell is a function of the level of power supplied to the electrolytic generating cell. In particular, by controlling the current supplied to each ozone generating cell, the concentration of ozone can be controlled. In the illustrative embodiment, the concentration of ozone controlled by ozone sanitation device 10 via the individual power signals 260 received by the electrical connector 250 and connected through to each respective ozone generating cell 210a-d.

An example of an ozone generating cell 210 suitable for use in cartridge 100 for generating aqueous ozone is an electrolytic cell, for example, as disclosed by U.S. Pat. No. 10,640,878 issued on May 5, 2020, which is hereby incorporated herein by reference. Alternative or improved electrolytic cells known in the art are also contemplated for ozone generating cell 210 for use with cartridge 100. Exemplary electrolytic ozone generating cells 210 provide a mechanical structure to guide a water flow across the surfaces of a perforated pair of electrodes, an anode and a cathode each framed by a current spreader, and separated by a proton exchange membrane (PEM) designed to conduct protons between the anode and cathode. An exemplary electrode can be constructed of boron-doped silicon or another suitable material. The boron doped silicon material serves as a conductor to pass current between the current spreader and boron doped, The doped silicon material may be about 200-800 microns thick, such as about 500 microns thick. The front side each electrode may have a boron-doped diamond coating or another suitable coating. The coating may be about 2-10 microns thick. The coating may be applied to the underlying silicon material by chemical vapor deposition (CVD) or another suitable deposition technique. The illustrative electrodes can be rectangular in shape, for example, having a width of about 8 millimeters and a length of about 10 millimeters, although the size and shape of the electrodes may vary, and are available from Neocoat SA of La Chaux-de-Fonds, Switzerland.

Figure 8B:
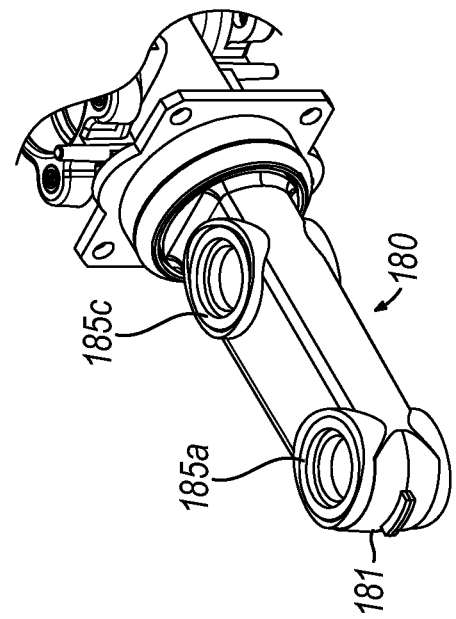
FIG. 8B is a perspective view of the inner conduit portion of the manifold portion of FIG. 8A.
Figure 8A:
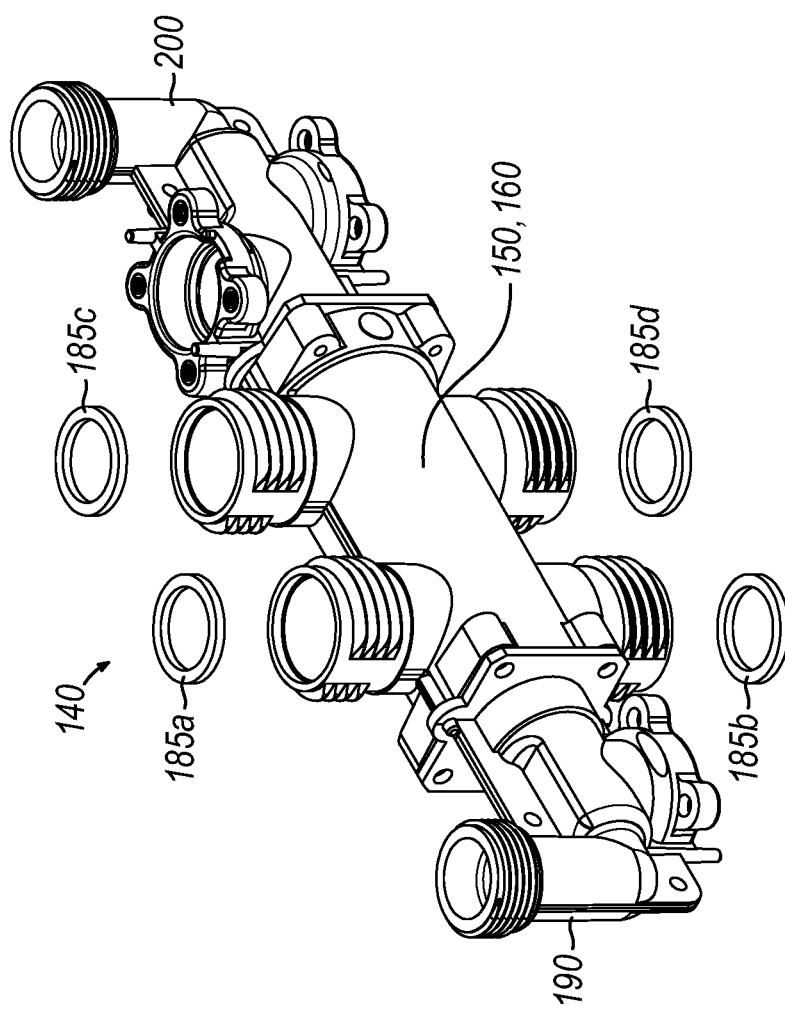
FIG. 8A is a perspective assembly view of the manifold portion of the ozone generator cartridge of FIG. 1.

As is illustrated in FIGS. 6 and 7, the coaxial arrangement defines an annulus 176 between the inner conduit 180 and the outer conduit 160. As shown in FIG. 8B, a first end 181 of the inner conduit 180 is closed off, which forcing the flow through water passageway 130 upon passing through the opening 164 of the outer conduit 160 and entering into a flow separation chamber 142 to separate into flows around the inner conduit and into annulus 176 defined between the exterior surface of the inner conduit and an interior surface of the outer conduit 160.

Figure 8D:
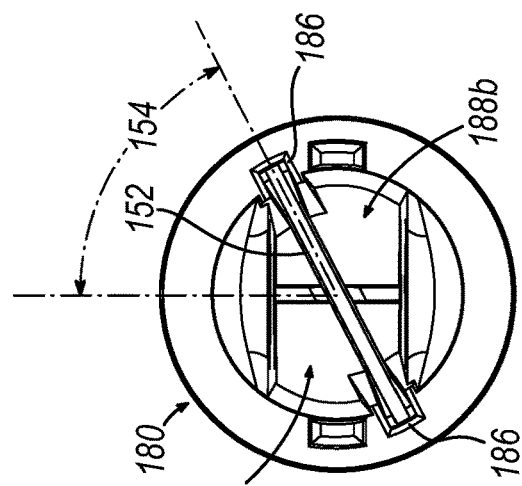
FIG. 8D is an end view of the coaxial central manifold portion of FIG. 8C.
Figure 8C:
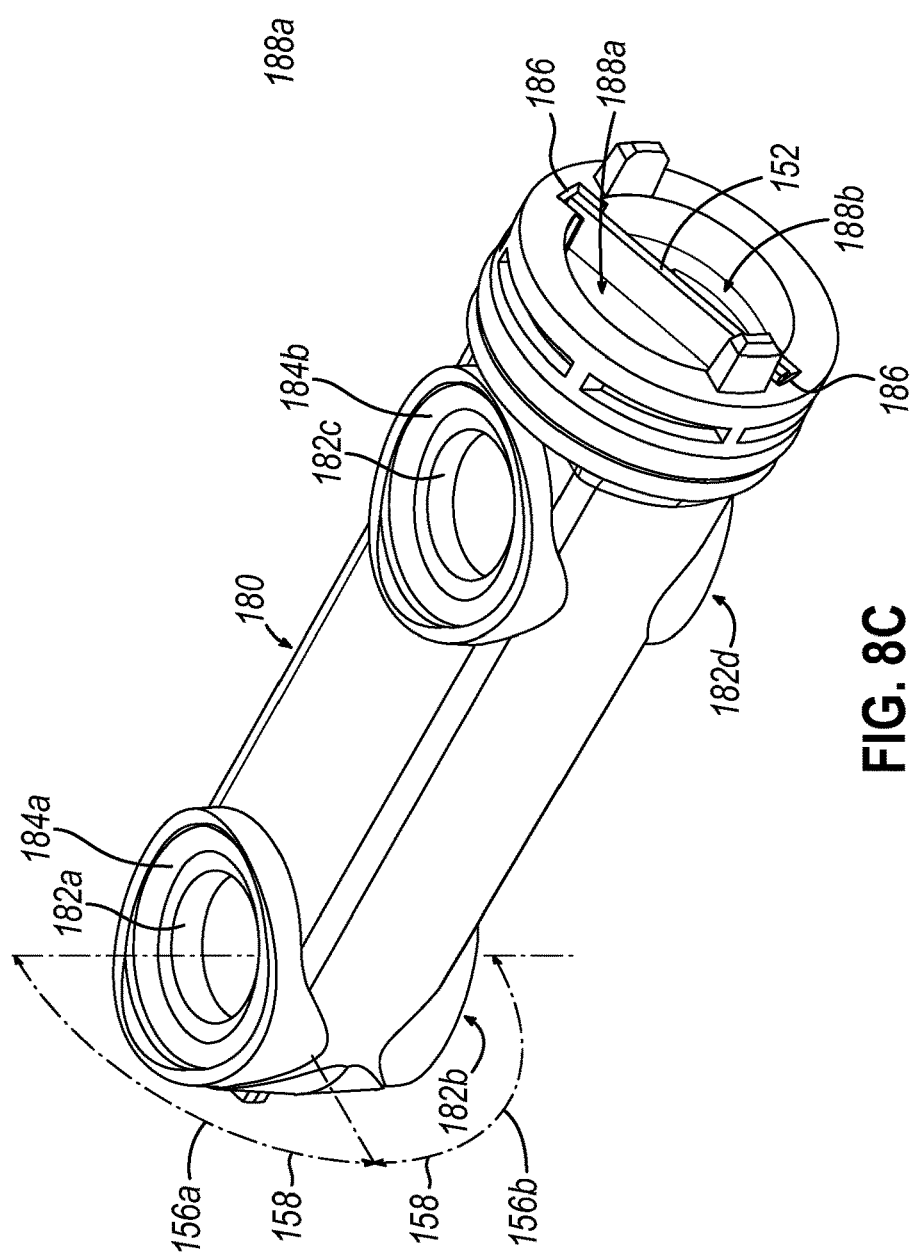
FIG. 8C is a perspective view of the coaxial central manifold portion of the ozone generator cartridge of FIG. 1.

Referring to FIGS. 6 and 8C, each ozone generating cell 210a-d define a cell inlet 214 in fluid communication with the annulus 176 and a cell outlet 216 in fluid communication with opening 182 of the inner conduit 180. The waterflow entering each cell inlet 214 becomes a separate parallel water passageway 302a-d portion of water passageway 300, each passing through the respective cell generating portion 212 of the respective one of ozone generating cells 210a-d and exiting cell outlet 216, through opening 182 and into inner conduit 180.

The generating portions 212a-d of the ozone generating cells 210a-d are fluidly sealed with a sealing surface 184a-d defined by the inner conduit 180, and optionally by a seal 185, for example a gasket, such that the only flow path out of annulus 176 for the water flow is through one of the generating portions 212a-d of the ozone generating cells 210a-d, as shown in FIG. 6 for parallel water passageways 302a-d.

This arrangement of the various components of central water passageway portion 150 and ozone generating cells 210a-d divides the waterflow through the water passageway 300 into a number of water passageways 302a-d that is that same as the number ozone generating cells 210 installed with manifold 140. Each of the parallel water passageways 302a-d enter the inner conduit 180 through the respective cell opening 182 defined by the inner conduit.

Another function of the parallel water passageways 302a-d arrangement is that by operating the parallel pathways and their associated ozone generating cells 210a-d simultaneously, a higher ozone concentration can be achieved for a given flowrate through the water passageway 300 than if the same number of ozone generating cells 210a-d were arranged in a serial water pathway arrangement, or than if ozone generating cells where operated alternately.

In this parallel arrangement, the water flowrate through each ozone generating cell 210a-d is divided by the number of cells/parallel water passageways 302a-d, for example, by four in the illustrative embodiment. By reducing the flow rate through each individual ozone generating cell 210a-d, in this case by one-quarter, the waterflow through each parallel water passageway is provided with a much higher ozone concentration for the same ozone generating cell output capacity and/or power level. If each parallel ozone generating cell 210a-d is controlled to deliver the same ozone concentration, no dilution will occur upon confluence and the water passageway 300 ozone concentration level will therefore be equally elevated. Although a serial arrangement could boost the ozone concentration at each successive ozone generating cells 210a-d, it has been found that a significant portion of the ozone generated by early cells in the series is lost in flowing through subsequent cells, for example, due to the waterflow experiencing added disturbances to the flow because of the serial flow arrangement, reducing the efficacy of the cumulative serial effect in boosting ozone concentration.

It is also thought that the parallel water passageways 302a-d arrangement can lengthen the duty life of the ozone generating cells 210a-d as each may be operated at a lower power to achieve the desired ozone concentration than if fewer cells were used, or if the cells were arranged serially. And if the desired ozone concentration can be achieved by powering a subset of the ozone generating cells, the duty life can be lengthened by alternating selectively powering only a subset of the cells. The latter may also be used to keep a cartridge in service that has suffered a degradation or failure of one of the ozone generating cells 210a-d as the load can be picked up by the remaining fully functional cells without changes to the hardware or water passageway 300.

In the illustrative embodiment, the ozone generator cells 210 can be driven by a range of at least 0-1.2 amps each, and with four ozone generator cells 210 each driven by a constant current of 410 milliamps, for example a buck-boost switching regulator, each aqueous ozone generator 100 produces a concentration of 0.8 ppm of aqueous ozone, with an observed typical voltage of 9-12 volts indicating normal ozone generator cell 210 operation. An elevated observed voltage, for example, 20-25 volts, or above 22 volts indicated degraded generator cell 210 operation. In detecting a degrading or degraded cell 210 in this way, operation of ozone generator 100 and device 10 may optionally continue by removing a degrading or degraded cell form operation and using only the non-faulted cells. Additionally, and optionally, a controller may store and/or communicate an alert message, for example, to a remote server, that an impending change of ozone generator 100 will be required.

Referring again to FIG. 4, the inner conduit 180 includes a baffle 152, which may partially or fully divide the interior of the inner conduit radially along at least a portion of its length. Referring to FIGS. 6, 8C and 8D, in the illustrated embodiment the baffle 152 defines a divider defining a first flow chamber 188a and a second flow chamber 188b, both extending along the entire length of the inner conduit 180.

Advantageously, the waterflow from parallel water passageways 302a and 302c is directed to the first flow chamber 188a, and the waterflow from parallel water passageways 302b and 302d is directed to the second flow chamber 188b. The waterflow separation provided by the baffle 152 significantly reduces the vortices and other flow disruptions within the interior chamber 180 that would otherwise be present from the confluence of opposite direction waterflows from water passageways 302a and 302b and from water passageways 302c and 302d, thereby reducing the loss of ozone concentration that would otherwise be induced.

Referring to FIG. 8D, to further reduce the disturbance of the waterflows exiting the ozone generating cells 210a-d and entering first and second flow chamber 188a-b, the baffle 152 can be oriented to an angle 154 that is nonorthogonal to the waterflow path entering from the ozone generating cells 210a-d, i.e., the longitudinal axis of the ozone generating cells. The baffle 152 may be coupled with the inner conduit 160 via baffle guides 187, for example, rails, or, baffle 152 may be molded integrally with the inner conduit.

In the illustrated embodiment of manifold 140, a flow confluence chamber 144 is defined adjacent a second end 187 of the inner conduit 180 and the inlet opening 206 of the outlet water passageway portion 200, approximately where baffle 152 terminates. Within the flow confluence chamber 144, the waterflows from the first and second flow chambers 188a-b, (separate parallel water passageway flows 302a-d) are recombined again into a single waterflow through water passageway 300 in the outlet water passageway portion 200.

The ozonate waterflow 25 through the outlet water passageways portion 200 passes over the surfaces of sensors 240a-b, for example oxidation reduction potential sensors as is disclosed above. By comparing ORP of ozonated waterflow 25 as measured by sensors 240a and 240b, with the untreated supply waterflow 23 as measured by sensor 230, the ozone concentration added to the water passageway 300 waterflow by the ozone generating cells 210 can be determined and ozone generating cells 210 can be individually and collectively controlled accordingly via power signals 260 to achieve a desired ozone concentration. Alternatively, the inlet sensor 230 could be eliminated and untreated supply waterflow 23 by sensor 240a with waterflow provided without energizing ozone generator cells 210 to baseline ORP for later comparison with ORP of ozonated water 52 measured by sensor 240a when the ozone generator cells 210 are energized. Yet another alternative is to for gall all ORP sensors 230 and 240a/b and to control the desired aqueous ozone concentration by setting the current level know to produce the specific concentration desired for the configuration of the generator 100 for a given flow rate, for example, 410 milliamps, for 3 gph, to provide 0.8 ppm aqueous ozone for the illustrative embodiment.

With brief reference to FIGS. 1 and 4, the inlet water passageway portion 190 defines a connector mount 194 for coupling the inlet connector 120 to the manifold 140. For example, the connector mount 194 may be a threaded coupling, compression coupling, adhesive joint, or other known standard or non-standard fluid coupling known in the art and suitable for the selected type of the water inlet connector 120. The outlet water passageway portion 200 defines a corresponding connector mount 204 at outlet opening 202 for the water outlet connector 130.

Referring to FIG. 7, an exploded cross-sectional view of the manifold 140 illustrates additional aspects of the illustrative embodiment. The inlet passageway portion 190 defines a sensor coupling 198 between the inlet opening 192 and the outlet opening 196 through which the sensor 230 can be releasably and sealingly coupled such that an electrode element 231 of the sensor 230 is disposed within the water passageway 300.

The sensor coupling 198 can be interoperable with a mount coupling 232 to provide releasable coupling of the sensor 230 with the inlet water passageway portion 190. In the illustrated embodiment, the mount coupling 232 is a mounting ring positionable over and around the sensor 230 to fasten with sensor coupling 198, for example using releasable fasteners, such as threaded fasteners. With releasable fasteners, the sensor 230 can be later detached for replacement if reconstruction of the cartridge 100 is later desired. The interface of the sensor 230, mount coupling 232, and the sensor coupling 198 may include sealing surfaces and/or sealing devices, for example gaskets or O-rings.

The sensor coupling 198 or another portion of inlet passageway portion 190 may also define a sensor alignment feature 199 that interacts with an alignment feature (not shown) of the sensor 230 to provide alignment of the electrode element 231 within the water passageway 300. For example, it is been found advantageous to align the element 231 so that the planar surface is parallel to the direction of waterflow within the water passageway 300, thereby reducing the magnitude of change in pressure, velocity, vortices, and other disturbances to fluid flow that would be induced if installed oblique or perpendicular to the waterflow direction.

The outlet water passageway portion 200 defines structures corresponding to those of inlet water passageway portion 190 discussed above, including connector mount 204 coupling water outlet connector 130 at outlet opening 202, sensor couplings 208a and 208b and engagement features 209a (not shown) and 209b, for respectively coupling outlet sensor 240a and 240b and orienting elements to 241a and 241b parallel to the water passageway 300 waterflow direction.

Minimizing of disturbances to waterflow is important for the ozonate waterflow 25 as it passes by sensor elements 241a and 241b, to provide a reliable differential measurement and therefore determination of ozone concentration provided by the ozone generating cells 210, and to reduce disturbances in waterflow that would reduce the ozone concentration. Therefore same orientation of the sensor elements 140a and 140b as for sensor element 231a is desired.

In the illustrative embodiment, the inlet water passageway portion 190 is coupled to the outer conduit 160 providing a fluid connection between the outlet opening 196 and the inlet opening 164. Features of an outlet coupling 197 and inlet coupling 162 which join portion 190 and conduit 160 together may provide a releasable coupling, for example, by using threaded fasteners or other releasable devices. The outlet coupling 197 and inlet coupling 162 may define ceiling surfaces using with or with sealing devices such as gaskets or O-rings, and may provide a support structure for the first end 181 of the inner conduit 180, as is illustrated in FIGS. 6 and 7.

In the illustrated embodiment, the outlet water passageway portion 200 is coupled to the outer conduit 160 and optionally to the inner conduit 180, providing a fluid connection between the flow confluence chamber 144 and the inlet opening 206. Additionally, features of the outlet coupling 166 and the inlet coupling 207 which join portion 200 and conduits 160 and 180 may provide a releasable coupling, for example, by using threaded fasteners or other releasable devices. The outlet coupling 166 and the inlet coupling 207 may define ceiling surfaces using with or with sealing devices such as gaskets or O-rings, and may provide a support structure for the second end 187 of the inner conduit 180 which also closes off and seals the annulus 176 adjacent the second end of the inner and outer conduits 160 and 180, as is best illustrated in FIG. 6.

Referring to FIGS. 4-7, each of the ozone generating cells 210a-d are releasably coupled with the central water passageway portion 150, for example with a cell mount coupling 170 defined by the outer conduit 160 and corresponding mount coupling 220 of the ozone generating cell 210a-d. For example, in the illustrated embodiment of the manifold 140, the cell mount couplings 170a-d of the outer conduit 160 are threaded pipe nipples extending about each of the coupling openings 172a-d. The corresponding mount couplings 220a-d in the illustrated embodiment comprises a corresponding threaded cap that with the mount couplings 170a-d, provide releasable coupling of the ozone generating cells 210a-d to the manifold 140. Advantageously, when secured, a portion of the ozone generating cells 210a-d, for example distal end of the generating portions 212a-d, each fluidly seals with the respective cell opening 182a-d of the inner conduit 180, for example against sealing surfaces 184a-d, and may use a seal 185a-d, for example, a gasket or O-ring.

An advantage of the cartridge 100 according to the present disclosure is how compactly ozone generating cells 210 and sensors 230 and 240 can be housed and coupled with the water passageway 300 for ozonating the waterflow. For example, by minimizing the length of the water passageway 300, losses in ozone concentration is minimized. One aspect of minimizing the length of the water passageway 300 is the coaxial arrangement of the central water passageway portion 150, including the parallel water passageways 302a-d arrangement that the coaxial arrangement enables. Another aspect of minimizing the length is locating more than one ozone generating cell 210 along the same circumferential arc 158 (defined by axes 156a-b), as illustrated in FIG. 7 and FIG. 8C. For example, cell mount coupling 170a is located at an angular axis 156a of +90 degrees along the circumferential arc 158, and cell mount coupling 170b is located at an angular axis 156b of −90 degrees along the circumferential arc 158. Optionally, additional ozone generating cells 210 can be located along the same circumferential arc 158, or alternatively or additional along the circumferential arc on which cell mount couplings 170c-d are located.

The various components of the manifold 140 may be constructed, for example molded from rigid materials not susceptible to breakdown from water and ozone, for example, polysulfone (PSU), polyvinylidene fluoride (PVDF), or 40% glass fiber reinforced polyphenylene sulphide (PPS). In other embodiments, the manifold 140 may be comprised of a unitary structure or a structure divided into portions or subcomponents differently than is described herein for the illustrative embodiment and as may be desirable for manufacturing, assembly, operational or reconstruction.

The electrical connector 250 can be electrically coupled to or mounted directly to a circuit board 252 and is coupled to an electrical connector 26 of the electrical system (not shown) of the ozone sanitation device 10. The circuit board 252 may include a memory device, for example for identification data for the cartridge 100 and/or the associated ozone sanitation device 10, or both, including for example a serial and/or model number and/or compatibility information between generators 100 and dispensing device 10, and pairing of a specific serial number generator with a specific serial number dispensing device. Additionally, the memory device 254 may enable data logging of usage, including lifespan, error detection, and information concerning individual instances of use. Lifespan data may include calibration information, specifications, elapsed or remaining usage of individual ozone generating cells 210 and/or the generator 100, including based on, for example, hours, gallons of water, ozone volume, total power, and the like. Data logging may include transmission of usage information through electrical connector 250, for example to a personal computing device and/or remote server, and/or for local storage in the memory device 254. Additionally, a security device 256 be included as a separate device, or as a feature of the memory device 254. Security device 256 may include encryption, blockchain, or other secure feature to authenticate the source of manufacturing, or reconstruction of the cartridge 100, or the pairing of cartridge 100 with a particular ozone sanitation device 10 or other connected devices The electrical connector 250 and circuit board 252 receive power signals 260 for driving the ozone generating cells 210a-d and powering for the sensors 230 and 240a-b, send sensor data signals 262 from the sensors, and send and/or receive security data signals 264 and logging data signals 266. In one embodiment, circuit board 252 includes a processor for providing control, security, data logging, or other functionality recited herein or otherwise known to a person of ordinary skill in the art for manufacturing, operating, repairing, and reconstructing the cartridge 100. An illustrative electrical connector and receptacle are the ET60S/ET60T signal and power combined series available from Samtec of New Albany, Ind.

Referring to FIG. 4, reconstruction of an expended generator cartridge 100 can include, for example, separating housing 102, removing and replacing all degraded components, for example, generator cells 210 and/or sensors 230 and 240, cleaning those and other remaining components that can be reused, replacing remaining components as required, reassembly and closing housing 102, rewriting memory and security devices 252, 254, 256, and calibration and/or testing, for example, verifying that the reconstructed generator 100 provides the desired aqueous ozone 25 concentration for water 23 provided at a given flowrate with the expected current and voltages levels for each of the generator cells 120, including proper operation of any sensors 230 and 240.

Referring to FIGS. 1 and 2B, plug-in coupling of the cartridge 100 into a corresponding docking receptacle 20 of the ozone sanitation device 10 requires proper orientation to ensure that the electrical connector 250 and the water inlet connector 120 and water outlet connector 130 are not reversed with the corresponding connectors of the docking receptacle. One or both of cartridge 100 and the docking receptacle 20 can include orientation features that prevent coupling if the orientation is incorrect. For example, an guidance or orientation feature 110 at a first end of the housing 102, in this example a recess or a protrusion, is located in the middle and the orientation features defined at an opposite end of the housing 102 (not shown) are located away from the middle. Corresponding guidance and/or orientation features 28 of the docketing receptacle 20 are interoperable with orientation features 110 to prevent plugging of the cartridge 100 into the docking receptacle 20 unless oriented and/or positioned correctly to result in proper water connections.

Alternatively, different size, shape, or other configuration of the water inlet connector 120 and the water outlet connector 130 and their associated connectors 20 and 24 of the docking receptacle 20 can be used to ensure proper orientation and prevent a reverse connection. Similarly, oriented mechanical features of the electrical connector 250 or the associated splash guard 107 could alternatively be used to ensure correct orientation. Housing 102 may also define recesses and/or protrusions, for example orientation features 110d to additionally or alternative operate with features of the docking station 20 to prevent improper orientation and reversed connections.

Figure 12B:
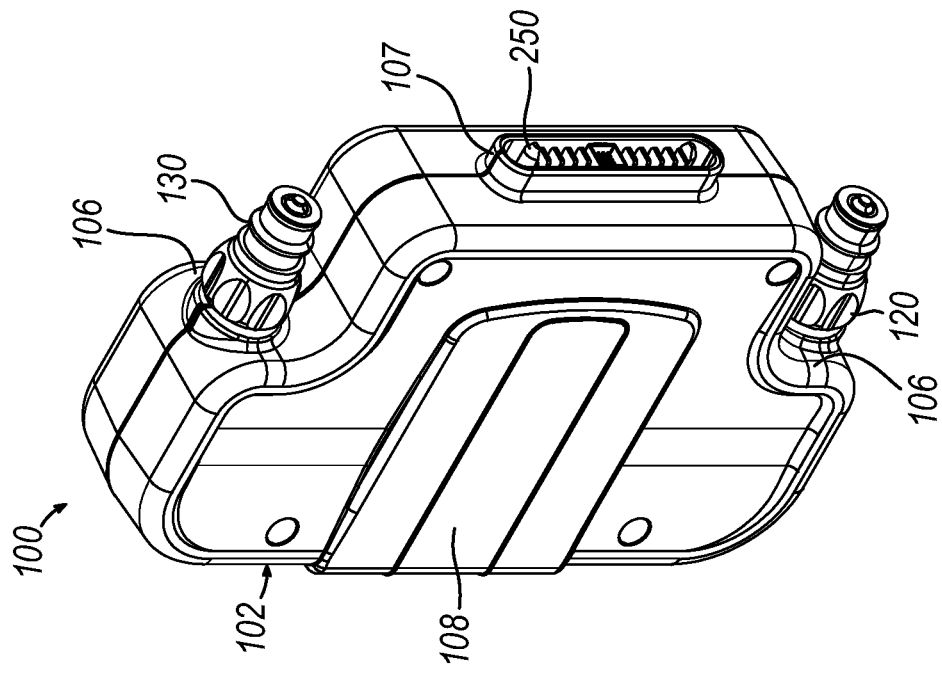
FIGS. 12A and 12b are perspective assembly views of a third embodiment of an ozone generator cartridge according to the present disclosure.

Advantageously, a splash guard 107 as illustrated in FIG. 12B may be defined by the housing 102 to the protect connector 250 from any water splashes resulting from plugging in or unplugging the cartridge 100 with the ozone sanitation device 10.

Referring to FIG. 1, to enable plugging and unplugging cartridge 100 into a docking receptacle 20 using a singular axis motion, the water inlet connector 120 defines a longitudinal axis 128 that is oriented parallel with a longitudinal axis 138 of the water outlet connector 130. The corresponding fixed water supply connector 22 and ozonated water connector 24 similarly are aligned and are properly spaced to engage connectors 120 and 130. A connection axis 258 of the electrical connector 250 is also farewell to the longitudinal axes 128 in 138 of the water connectors 120 and 130.

Advantageously, each of the three pair of connectors, 22 and 120, 24 and 130, and 250 and 26 are selected to enable pluggable engagement using a singular direction of motion, for example, along longitudinal axis 128, 138, and 258, to engage all of the corresponding connectors simultaneously and without further action other than moving the cartridge manually into position in the direction along the referenced parallel axes.

Additionally, and advantageously, a locking mechanism 116 of the cartridge 100 can operably cooperate with a locking mechanism 30 of the docking receptacle 20 so that cartridge 100 auto-locks into position relative to the docking receptacle 20, ensuring corresponding connectors 120 and 22, 130 and 24, and 250 and 26 remain engaged. A release mechanism 32 associated with the docking receptacle or a release mechanism 118 associated with the cartridge 100 can be manually actuated to disengage locking mechanisms 30 and 100. The connector pairs used for 120 and 22 and/or 130 and 24 can be selected to be valved auto-locking fluid connectors as are known in the art.

For example, the water connector 22 may include locking clips that automatically spring into position when engaged and engagingly interfere with an engagement feature 126 of the water inlet connector 120, thereby fluidly coupling the connectors 22 and 122 until manually released by the release mechanism 32 or 118. The release mechanism 32 or 118 can move the locking clips to a disengaged position, allowing the cartridge 100 to be pulled along axes 128, 258, and 138, disengaging the connector pairs and allowing the cartridge 100 to be removed from the docking receptacle 30, for example, to be replaced with a new or reconstructed cartridge 100. For example, commercially available connectors such as valved coupling insert part number HFCD261235BSPP and valved panel mount coupling body part number HFCD16835V, both available from Colder Product Company of Saint Paul, Minn.

Advantageously, the opening 122 of the water connector 120 can be sealed by a spring biased valve 124 when connector 120 is disengage from the water supply connector 22, thereby retaining water within the manifold 140. Similarly, the opening 132 of the water connector 130 can be sealed by a spring biased valve 134 when connector 130 is disengaged from corresponding connector 24, thereby retaining water within the manifold 140. The sealing by valves to retain water within manifold 140 can be advantageous when one or more sensors must remain wetted to avoid degrading.

Figure 12A:
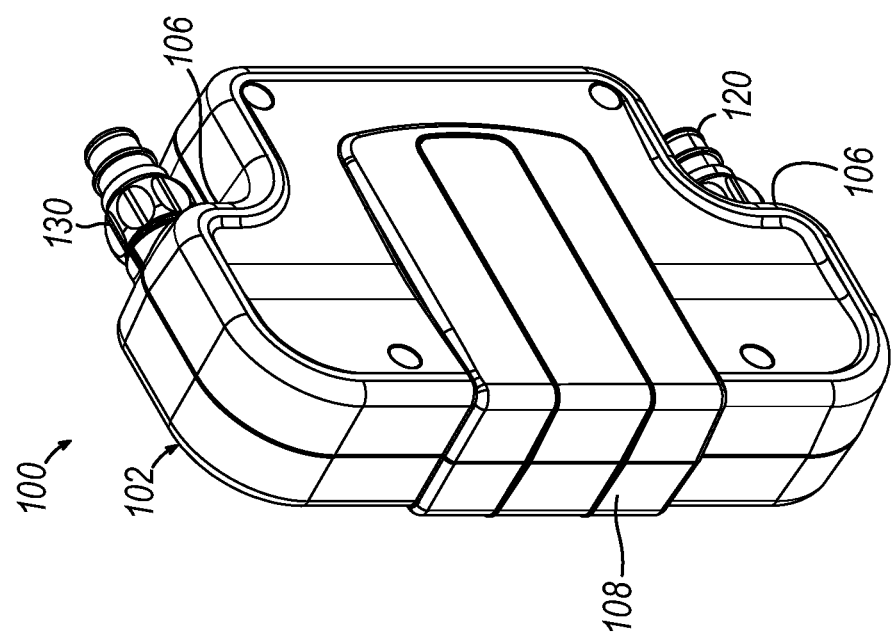

Advantageously, as illustrated in FIGS. 9 and 12A-B, the housing 102 may define recesses or other features to aid in grasping and holding cartridge 100, for example, with a single hand. For example, housing 102 defines a finger hold 108a on a first side and a thumb hold 108b on an adjacent side, thereby facilitating the plugging and unplugging of cartridge 100 with docking receptacle 20.

Relating to ensuring proper ozone concentration is provided, it is important to ensure that components of cartridge 100 that are manufactured to specification, tested, and calibrated before being put into service are not tampered with or replaced with incompatible, untested or noncalibrated components to would prevent improper ozone concentration from being detected by the ozone sanitation device 10 cartridge 100 is used with. Therefore, access to the housing 102 may be limited by or detectable by security features.

Referring to FIG. 1, the housing 102, including housing sides 104a and 104b, may be secured together by various means known in the art, including releasably with securing feature 112, for example, threaded fasteners, or permanently secured, for example using an adhesive, via molding, or the like. If releasably secured, as is the case for the illustrative embodiment, a tampering device 114 may be associated with the housing 102. For example, the housing 102 or contents therein may include a frangible portion. Additionally or alternatively, a tamper evident label may be positioned over one or more of security features 112 that must be accessed to open the housing 102. Additionally or alternatively, a digital device, for example the security device 256 of the circuit board 252, shown in FIG. 3, may be configured to electromechanically or electrooptically detect tampering, particularly the separating of the housing sides 104a and 104b. For example, the security device 256 can prevent use with the ozone sanitation device 10 after lifetime usage or an error is detected and stored, or if tampering is detected and stored. Alternatively or additionally, the security device 256 may prevent the cartridge 100 from by used with a device 10 different than the one for which it was prepared.

In one embodiment, in the absence of a sensor 130 and 240a-b populating one or more of the sensor mounts 198 and 208a-b, the mount is populated with a sealing plug 228 to fluidly seal the manifold 140. Similarly, in one embodiment, for example embodiments requiring a lower cost or a lower ozone concentration, one or more of the cell mount couplings 170a-d is populated with a sealing plug 228, which provides a seal across opening 172a-d and 182a-d, thereby closing off one or more of the parallel water passageways 302a-d and ensuring a waterflow through the water passageway 300 flow through one of the ozone generating cells 210a-d.

While the invention has been illustrated and described in detail in the foregoing drawings and description, the same is to be considered as illustrative and not restrictive in character, it being understood that only illustrative embodiments thereof have been shown and described and that all changes and modifications that come within the spirit and scope of the invention as defined in the claims and summary are desired to be protected.

| REFERENCE NUMERAL LISTING | | | |
|---|---|---|---|
| 10 | aqueous ozone delivery device | 130 | aqueous outlet connector |
| 12 | sanitizing cavity | 132 | opening |
| 14 | aqueous ozone delivery outlet | 134 | valve |
| 20 | docking receptacle | 136 | engagement feature |
| 22 | water supply connector | 138 | longitudinal axis |
| 23 | untreated supply water | 140 | manifold |
| 24 | ozonated water connector | 142 | flow separation chamber |
| 25 | ozonated water | 144 | flow confluence chamber |
| 26 | electrical connector | 150 | coaxial water passageways portion |
| 28 | orientation feature | 152 | baffle / divider |
| 30 | locking mechanism | 154 | nonorthogonal angle |
| 32 | release mechanism | 156 | angular axes |
| 100 | cartridge | 158 | circumferential arc |
| 102 | housing | 160 | outer conduit |
| 104a-b | housing side | 162 | inlet coupling |
| 105a-b | component supports | 164 | inlet opening |
| 106 | connector recess | 166 | outlet coupling |
| 107 | splash guard | 168 | outlet opening |
| 108a-b | finger / thumb holds | 170a-d | cell mount coupling |
| 110 | orientation features | 172a-d | cell coupling opening |
| 112 | securing feature | 176 | annulus |
| 114 | anti-tamper device | 180 | inner conduit |
| 116 | locking mechanism | 181 | first end |
| 118 | release mechanism | 182a-d | cell opening |
| 120 | water inlet connector | 184 | cell sealing surface |
| 122 | opening | 185a-d | seal |
| 124 | valve | 186 | baffle mount |
| 126 | engagement feature | 187 | second end |
| 128 | longitudinal axis | 220a-d | mount coupling |
| 188a-b | first/second flow chamber | 228 | sealing plug |
| 190 | inlet water passageways portion | 230 | inlet sensor |
| 192 | inlet opening | 231 | sensor element |
| 194 | connector mount | 232 | coupling |
| 196 | outlet opening | 240a-b | outlet sensors |
| 197 | outlet coupling | 241a-b | sensor elements |
| 198 | sensor coupling | 242a-b | mounting coupling |
| 199 | sensor alignment feature | 250 | electrical connector |
| 200 | outlet water passageways portion | 252 | circuit board |
| 202 | outlet opening | 254 | memory device |
| 204 | connector mount | 256 | security device |
| 206 | inlet opening | 258 | connection axis |
| 207 | inlet coupling | 260 | power signal |
| 208a-b | sensor couplings | 262 | sensor data signal |
| 209b | sensor alignment feature | 264 | security data signal |
| 210a-d | ozone generating cells | 266 | logging data signal |
| 212 | generating portion | 300 | water passageway |
| 214a-d | cell inlet | 302a-d | parallel water passageways |
| 216a-d | cell outlet | | |

The invention claimed is:

1. An aqueous ozone generator cartridge, comprising:
a water inlet for supplying water to the cartridge;
a water outlet for expelling aqueous ozone from the cartridge;
a water treatment manifold including a coaxial water passageways portion having an inner conduit located within an outer conduit, one of the inner and outer conduits fluidly coupled to the water inlet, and the other of the inner and outer conduit fluidly coupled to the water outlet; and
at least one ozone generating cell having a generating portion located outside the inner conduit and fluidly coupled with the inner and outer conduits to enable the manifold to provide waterflow through the generating portion of each of the at least one ozone generating cells.

2. The aqueous ozone generator cartridge of claim 1, wherein
the manifold defines:
a flow separation chamber to supply a plurality of water pathways through the at least one ozone generating cells; and
a flow confluence chamber to rejoin the plurality of water pathways into a single water pathway.

3. The aqueous ozone generator cartridge of claim 1, wherein the manifold and the at least one ozone generating cells together define parallel water pathways whereby water flowing from the water inlet to the water outlet passes through only one of the at least one ozone generating cells.

4. The aqueous ozone generator cartridge of claim 3, wherein the inner and outer conduits each define a plurality of pairs of openings for fluidly coupling the at least one ozone generating cells.

5. The aqueous ozone generator cartridge of claim 4, wherein at least two pairs of the plurality of pairs of openings are angularly displaced along the same circumferential arc of the coaxial water passageways portion, thereby minimizing a length of the manifold.

6. The aqueous ozone generator cartridge of claim 4, wherein at least one of the plurality of pairs of openings is populated with a fluidly sealing plug instead of one of the at least one ozone generating cells.

7. The aqueous ozone generator cartridge of claim 1, wherein a plurality of water pathways defined between the water inlet and the water outlet are operably fixed.

8. The aqueous ozone generator cartridge of claim 1, wherein:
   each of the at least one ozone generating cells includes a cell inlet for receiving water, each cell inlet is fluidly coupled to a space between the inner and outer conduits; and
   each of the at least one ozone generating cells includes a cell outlet for expelling water, each cell inlet is fluidly coupled to the inner conduit.

9. The aqueous ozone generator cartridge of claim 8, wherein:
   the space between the inner and outer conduits defines an annulus fluidly coupled to the water inlet; and
   the inner conduit is fluidly coupled to the water outlet.

10. The aqueous ozone generator cartridge of claim 9, wherein a segment of every one of the plurality of water pathways defined between the annulus and the inner conduit each pass through at least one of the at least one ozone generating cells.

11. The aqueous ozone generator cartridge of claim 1, wherein the inner conduit includes a baffle to reduce waterflow turbulence.

12. The aqueous ozone generator cartridge of claim 11, wherein the orientation of the baffle is nonorthogonal relative to ozonated water flowing from each of the at least one ozone generating cell and into the inner conduit.

13. The aqueous ozone generator cartridge of claim 11, wherein the baffle is a divider fluidly separating at least a portion of the length of the inner conduit into a first flow area and a second flow area, whereby each of the first and second flow areas receive ozonated waterflow from a subset of the at least one ozone generating cells.

14. The aqueous ozone generator cartridge of claim 1, further comprising a first oxidation-reduction potential sensor fluidly coupled to the manifold and located between the coaxial water passageways portion of the manifold and the water outlet.

15. The aqueous ozone generator cartridge of claim 14, further comprising a second oxidation-reduction potential sensor fluidly coupled to the manifold and located between the coaxial water passageways portion of the manifold and the water inlet.

16. The aqueous ozone generator cartridge of claim 15, further comprising a housing, and wherein the housing encloses the manifold, the at least one ozone generating cells, and first and second oxidation reduction potential sensors.

17. The aqueous ozone generator cartridge of claim 15, further comprising a third oxidation-reduction potential sensor fluidly coupled to manifold and located between the first oxidation-reduction potential sensor and the water outlet.

18. The aqueous ozone generator cartridge of claim 1, further comprising a housing enclosing the water treatment manifold and the at least one ozone generating cell, and wherein the housing can be opened to reconstruct the aqueous ozone generator cartridge by replacing the at least one ozone generating cell.

19. An aqueous ozone generator cartridge, comprising:
   an electrical connector;
   a water inlet for supplying water to the cartridge;
   a water outlet for expelling aqueous ozone from the cartridge;
   a water treatment manifold fluidly coupled to the water inlet and the water outlet;
   a housing enclosing the water treatment manifold; and
   a plurality of ozone generating cells located within the housing and having a generating portion receiving a power signal from the electrical connector and fluidly coupled with the water treatment manifold to provide a plurality of water pathways, each of the plurality of water pathways flows through the generating portion of only one of the plurality of ozone generating cells; and
   wherein the plurality of water pathways are fluidly parallel and operably fixed.

20. The aqueous ozone generator cartridge of claim 19, further comprising a first sensor fluidly coupled to the manifold, measuring an attribute of the water altered by the plurality of ozone generating cells, and providing a data signal to the electrical connector.

21. The aqueous ozone generator cartridge of claim 19, further comprising a memory device enclosed by the housing and electrically coupled with the electrical connector and wherein the memory device enables at least one of cartridge usage data logging and storage of cartridge identity data.

22. The aqueous ozone generator cartridge of claim 19, further comprising a security device authenticating at least one of a manufacturer and a reconstructor of the cartridge.

23. An aqueous ozone generator cartridge, comprising:
   a water inlet for supplying water to the cartridge;
   a water outlet for expelling aqueous ozone from the cartridge;
   a water treatment manifold including a coaxial water passageways portion having an inner conduit located within an outer conduit, one of the inner and outer conduits fluidly coupled to the water inlet, and the other of the inner and outer conduit fluidly coupled to the water outlet; and
   at least one ozone generating cell having a generating portion located outside the inner conduit and fluidly coupled with the inner and outer conduits to enable the manifold to provide waterflow through the generating portion of each of the at least one ozone generating cells; and
   wherein water pathways defined by the water treatment manifold and at least one ozone generating cell between the water inlet and the water outlet are fluidly parallel and operably fixed.

* * * * *